(12) United States Patent
Ling et al.

(10) Patent No.: US 7,679,082 B2
(45) Date of Patent: Mar. 16, 2010

(54) MULTI-FUNCTIONAL COPOLYMERS COMPRISING RARE EARTH METAL COMPLEXES AND DEVICES THEREOF

(76) Inventors: Qidan Ling, c/o National University of Singapore, 10 Kent Ridge Crescent, Singapore 119260 (SG); Wei Huang, 220 Handan Road, Shanghai 200433 (CN); En-Tang Kang, 9, Begonia Crescent, Singapore 809978 (SG); Koon Gee Neoh, c/o National University of Singapore, 10 Kent Ridge Crescent, Singapore 119260 (SG)

( * ) Notice: Subject to any disclaimer, the term of this patent is extended or adjusted under 35 U.S.C. 154(b) by 282 days.

(21) Appl. No.: 11/718,976

(22) PCT Filed: Nov. 10, 2005

(86) PCT No.: PCT/SG2005/000384
§ 371 (c)(1),
(2), (4) Date: May 9, 2007

(87) PCT Pub. No.: WO2006/052222
PCT Pub. Date: May 18, 2006

(65) Prior Publication Data
US 2007/0290199 A1 Dec. 20, 2007

(51) Int. Cl.
H01L 51/30 (2006.01)
C07D 221/00 (2006.01)
C07F 9/28 (2006.01)
C08G 61/12 (2006.01)
C09K 11/06 (2006.01)

(52) U.S. Cl. .................. 257/40; 257/E51.001; 313/504; 528/363; 528/391; 528/396; 528/401; 528/422; 528/423; 546/10; 546/4; 556/21

(58) Field of Classification Search .................. 257/40, 257/E51.001; 313/504; 528/363, 391, 396, 528/401, 403, 422, 423; 546/10, 4; 556/21
See application file for complete search history.

(56) References Cited

U.S. PATENT DOCUMENTS 6,148,142 A 11/2000 Anderson

FOREIGN PATENT DOCUMENTS

| EP | 0443861 | 8/1991 |
|----|---------|--------|
| JP | 63-070257 | 3/1988 |
| JP | 63-175860 | 7/1988 |
| JP | 02-135359 | 5/1990 |
| JP | 02-135361 | 5/1990 |
| JP | 02-209988 | 8/1990 |
| JP | 03-037992 | 2/1991 |
| JP | 03-152184 | 6/1991 |
| JP | 2000-327715 | 11/2000 |
| JP | 2003-332075 | 11/2003 |
| WO | WO-90-13148 | 11/1990 |
| WO | WO-02-43446 | 5/2002 |
| WO | WO-2004-015025 | 2/2004 |
| WO | WO-2004092185 A1 * | 10/2004 |

OTHER PUBLICATIONS

Zhang, M. et al "Metal Ionochromic Effects of Conjugated Polymer: Effects of the Rigidity of Molecular Recognition Sites on Metal Sensing" in Journal of Physical Chemistry B vol. 107, pp. 6535-6538 published online Jun. 11, 2003.*
Liu, B.. et al "Design and Synthesis of Bipyridyl-Containing Conjugated Polymers:Effects of Polymer Rigidity on Metal Ion Sensing" in Macromolecules vol. 34, pp. 7932-7940, published online Oct. 9, 2001.*
Yasuda, T. et al "A New Soluble 1, 10-Phenanthroline-Containing π-Conjugated Polymer: Synthesis and Effect of Metal Complexation on Optical Properties" in Advanced Materials vol. 15 pp. 293-296, published Feb. 5, 2003.*
Qidan Ling, et al, "PL and EL properties of novel Eu-containing copolymer" *Thin Solid Films*, vol. 417 (2002), pp. 127-131.
Jian Pei, et al "Efficient energy transfer to achieve narrow bandwidth red emission from $Eu^{3+}$ grafting conjugated polymers" *Macromolecules*, vol. 35, (2002) pp. 7274-7280.

* cited by examiner

*Primary Examiner*—Irina S Zemel
*Assistant Examiner*—Jeffrey Lenihan
(74) *Attorney, Agent, or Firm*—Schwabe, Williamson & Wyatt, P.C.

(57) ABSTRACT

The invention relates to copolymer complexes of the formula (I):

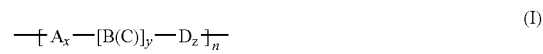

wherein $[A_x\text{-}[B(C)]_y\text{-}D_z]$ denotes a single unit of the copolymer complex that is repeated n times, wherein n is an integer greater than one, and wherein the single unit comprises a conjugated backbone coordinated to a complex (C) comprising rare earth metal(s); x, y and z are numbers greater than zero such that x=y+z; A is independently selected from a group consisting of: fluorene, carbazole, oxadiazole, triphenylamine or derivatives thereof; B is a functional ligand selected from the group consisting of: benzoic acid, 1,3-diphenylpropane-1,3-dione, 1,10-phenanthroline, 2,2-bipyridine, or derivatives thereof; and D is independently selected from a group consisting of: fluorene, carbazole, oxadiazole, triphenylamine or derivatives thereof.

49 Claims, 3 Drawing Sheets

MULTI-FUNCTIONAL COPOLYMERS COMPRISING RARE EARTH METAL COMPLEXES AND DEVICES THEREOF

FIELD OF THE INVENTION

The present invention is in the general field of materials chemistry and relates to a series of copolymers comprising rare earth metal complexes, methods for preparation thereof and use of the copolymer complexes.

BACKGROUND OF THE INVENTION

Light-emitting devices (LEDs) comprising conjugated polymers have become a topic of great interest since the first demonstration of an efficient polymer light-emitting diode. A large variety of polymers, copolymers, and their derivatives have been shown to exhibit electroluminescent properties. Single layer polymer LEDs are typically constructed by sandwiching a thin layer of luminescent conjugated polymer between two electrodes composed of an anode and a cathode, wherein at least one electrode is either transparent or semi-transparent.

Light-emitting layers in the form of a film of a conjugated polymer are used in electroluminescence devices. Examples of such devices are described in WO 90/13148 and EP-A 0 443 861. The configurations of these devices may consist of a simple single layer, bilayers, or blends used to enhance efficiency and tune the emission wavelength, or multilayers that may allow the device to be operated under an applied voltage.

Although good results have been obtained with the application of conjugated polymers in devices, the purity of the emission colour, in particular, is still unsatisfactory. Full colour displays require pure red, green, and blue emission. Obtaining monochromatic emission from conjugated polymers or small organic molecules is still difficult, since their emission spectra typically have a line width (full width at half maximum, or FWHM) of 50-200 nm, arising from inhomogeneous broadening and vibronic progression. Furthermore, in conjugated molecules, light is only generated from the singlet excitons, while the triplet excitons are lost in the non-radiative transitions. From spin statistics, since only 25% of the excitons in conjugated molecules have singlet character, the quantum efficiency of a conjugated polymer LED cannot exceed 25%.

In attempting to optimise monochromatic emission, a great deal of effort has been devoted to the application of rare earth complexes in organic LEDs. Rare earth compounds are excellent chromophores that exhibit intense fluorescence with a narrow spectral bandwidth (FWHM of 5 to 20 nm) and relatively long decay lifetime ($10^{-2}$ to $10^{-6}$s). They are the most widely used materials in CRT displays and inorganic LEDs.

However, the organic LEDs, especially the single-layer LEDs, based on rare earth complexes show relatively low efficiency as well as poor performance. These phenomena may be attributed to the poor ability of organic LEDs to transport charge carriers and inefficiency in energy transfer. Additionally, many of the low molecular weight rare earth complexes undergo decomposition to some extent during film formation by vacuum deposition. Decomposition of the rare earth complexes can be avoided in spin-coated films containing the rare earth complexes dispersed in polymer matrices. A drawback of this technique, however, is that non-uniform blending or dispersion of the dopants may result in phase separation and ionic aggregation.

WO 02/43446, JP 2000327715, and U.S. Pat. No. 6,148,142 describe polymeric compounds, wherein rare earth complexes are either blended or doped with the polymers, or chelated to non-conjugated polymers. However, these polymers have several drawbacks such as low efficiency and broad emission bands.

Accordingly, there is a need in this field of technology of improved and more efficient polymers, for example, polymers having improved semi-conductive properties and/or mechanical flexibility.

SUMMARY OF THE INVENTION

The present invention provides a copolymer complex of the formula (I):

wherein $[A_x\text{-}[B(C)]_y\text{-}D_z]$ denotes a single unit of the copolymer complex that is repeated n times, wherein n is an integer greater than one, and wherein the single unit comprises a conjugated backbone coordinated to a complex (C) comprising rare earth metal(s), x, y and z are numbers greater than zero such that x=y+z; A is a group comprising at least one of fluorene, carbazole, oxadiazole, triphenylamine or derivatives thereof; B is a functional ligand selected from the group consisting of: benzoic acid, 1,3-diphenylpropane-1,3-dione, 1,10-phenanthroline, 2,2-bipyridine, and derivatives thereof; and D is independently different from A and is independently selected a group consisting of: fluorene, carbazole, oxadiazole, triphenylamine or derivatives thereof.

The copolymer complex according to the invention may be a random or block copolymer complex. In particular, D may be different from A at each occurrence.

The group A may be represented by the formula:

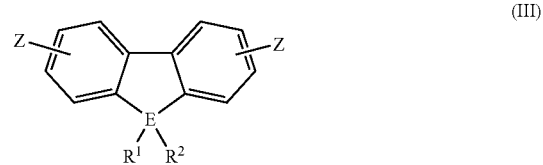

wherein $R^1$ and $R^2$ are the same or different and are linear or branched $C_{1-20}$ alkyl or alkoxy groups or at least one of $R^1$ and $R^2$ is absent, Z is a point of connection to a further block of the copolymer, E is a carbon atom (C) or a nitrogen atom (N), and when E is a nitrogen atom, Z is at positions 3 and 6, and when E is a carbon atom, Z is at positions 2 and 7. In particular, when A is a fluorene group, E may be a carbon atom and $R^1$ is the same as $R^2$. When A is a carbazole group, E may be a nitrogen atom and $R^2$ is absent. $R^1$ and $R^2$, may be independently selected from the group consisting of: n-hexyl group, 2-ethylhexyl group, n-octyl group, n-decyl group, n-dodecyl group, 2-hexyldecyl group, n-octadecyl and corresponding alkoxyl groups.

In particular, [B(C)] is an organic complex, and C is represented by the formula:

wherein M is a rare earth metal ion; $L^1$ is an enolate, carboxylate, sulfonate, alkoxide, or amide ligand; $L^2$ is a neutral ligand selected from the group consisting of 1,10-phenanthroline (phen), 2,2-bipyridine group (bpy), 2,6-di(pyridine-3-yl)pyridine (tpy), phosphine oxide and derivatives thereof; a is an integer in the range of 2-4; and b is 0 or 2. For example, [B(C)] may be represented by the formula:

(VIII)

wherein M is an independent rare earth ion, $L^1$ is selected from the group consisting of: enolate, carboxylate, sulfonate, alkoxide, amide ligands and derivative thereof; a is an integer in the range of 2-4.

B may be a derivative of the 1,10-phenanthroline or 2,2-bipyridine group of the Formulae:

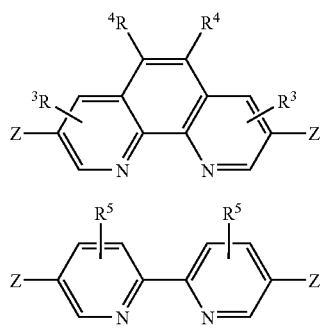

(XV)

(XVI)

$R^3$, $R^4$, and $R^5$ are independent groups selected from the group consisting of: hydrogen, alkyl, perfluoroalkyl, alkoxy, aryl and aryloxy groups; and Z is a point of connection to a further block of the copolymer at positions 3 and 8 on 1,10-phenanthroline and 2,2-bipyridine groups.

The organic complex [B(C)] may be selected from the group consisting of:

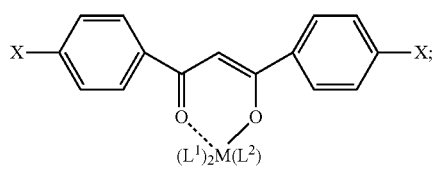

(IX)

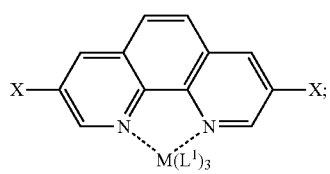

(X)

(XI)

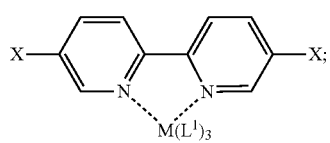

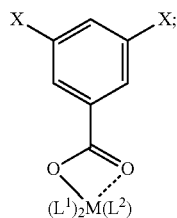

(XII)

and wherein X is independently in each occurrence a halide; M is a rare earth metal ion; $L^1$ is an enolate, carboxylate, sulfonate, alkoxide, or amide ligand; $L^2$ is an independent neutral ligand selected from the group comprising 1,10-phenanthroline (phen), 2,2-bipyridine group (bpy), 2,6-di(pyridine-3-yl)pyridine (tpy), phosphine oxide and derivatives thereof.

M may be a rare earth metal ion selected from the group consisting of: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu), scandium (Sc) and yttrium (Y).

D may be selected from the group consisting of a derivative of oxadiazole and a derivative of triphenylamine of the following formulae:

(V)

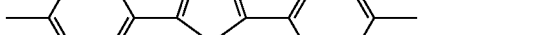

(VI)

wherein $R^8$ is independently selected from the group consisting of: hydrogen, alkyl, perfluoroalkyl, alkoxy, aryl and aryloxy groups; $R^9$ is independently selected from hydrogen, alkyl, alkoxy, carboxyalkyl or carboxyaryl, wherein $R^8$ or $R^9$ is $C_{1-20}$ and b is an integer in the range of 0 to 3.

The present invention also provides copolymer complexes of the formula:

(II)

wherein n is an integer greater than one, and wherein the single unit $[A_x\text{-}B_y\text{-}D_z]$ represent comprises a conjugated backbone, x, y and z are numbers greater than zero such that x=y+z; A is a group comprising at least one of fluorene, carbazole, oxadiazole, triphenylamine or derivatives thereof; B is a functional ligand selected from the group consisting of: benzoic acid, 1,3-diphenylpropane-1,3-dione, 1,10-phenanthroline, 2,2-bipyridine, or derivatives thereof; and D may be the same or different to A and is a group comprising at least one of fluorene, carbazole, oxadiazole, triphenylamine or derivatives thereof. The copolymer complex may be a random or block copolymer complex.

The present invention relates also to a method of producing a copolymer complex of Formula (I), comprising synthesizing a conjugated backbone $[A_x\text{-}B_y\text{-}D_z]$, and post-chelation of the backbone to a rare earth complex C comprising a rare earth ion and co-ligands.

In particular, the conjugated backbone may be synthesized by reaction of a dihalide with a diboronate or diboronic acid in a Suzuki reaction.

Polymeric materials such as films and layers comprising the copolymer complexes of the present invention as well as devices comprising polymeric materials thereof are also presented.

DETAILED DESCRIPTION OF THE INVENTION

Figure 1:
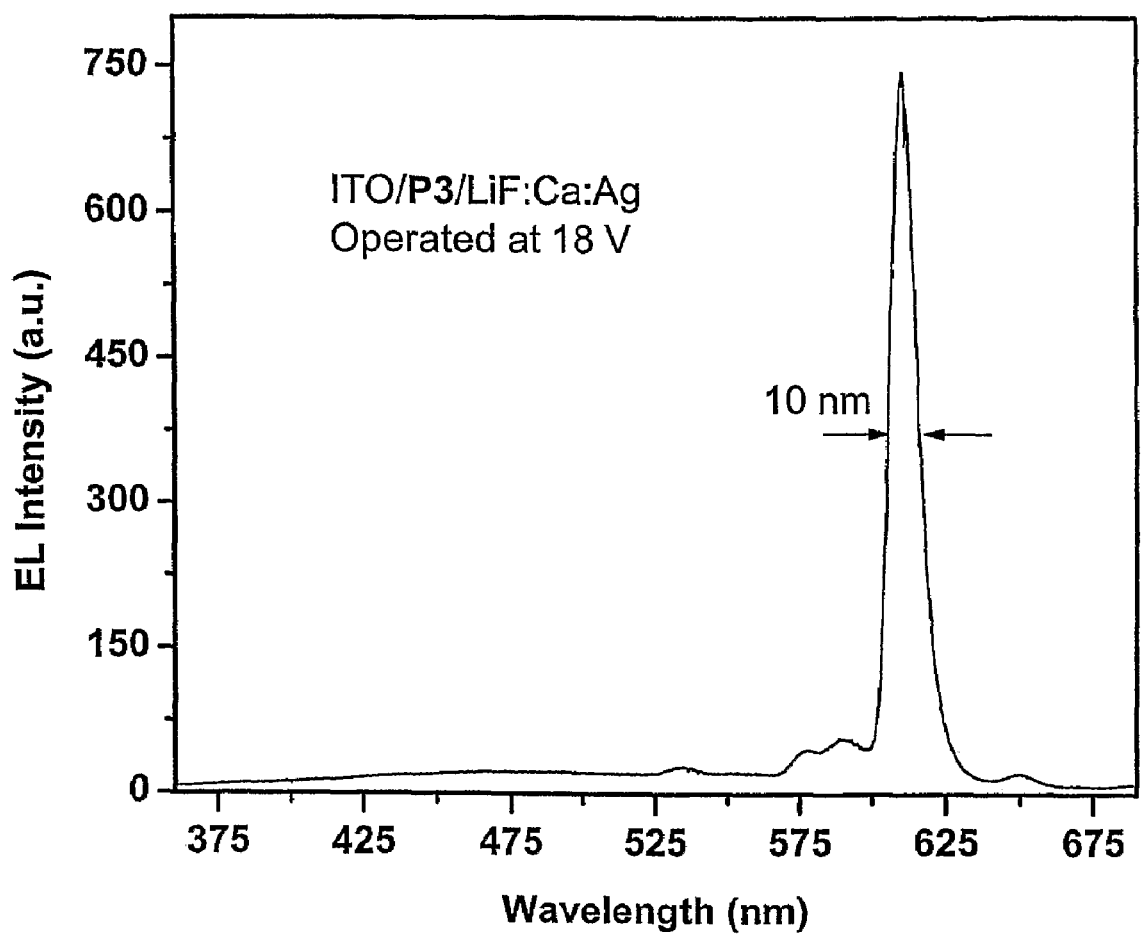
FIG. 1. Electroluminescence spectrum of the single-layer PLED, showing the monochromatic emission properties with the FWHM of only 10 nm.
Figure 2:
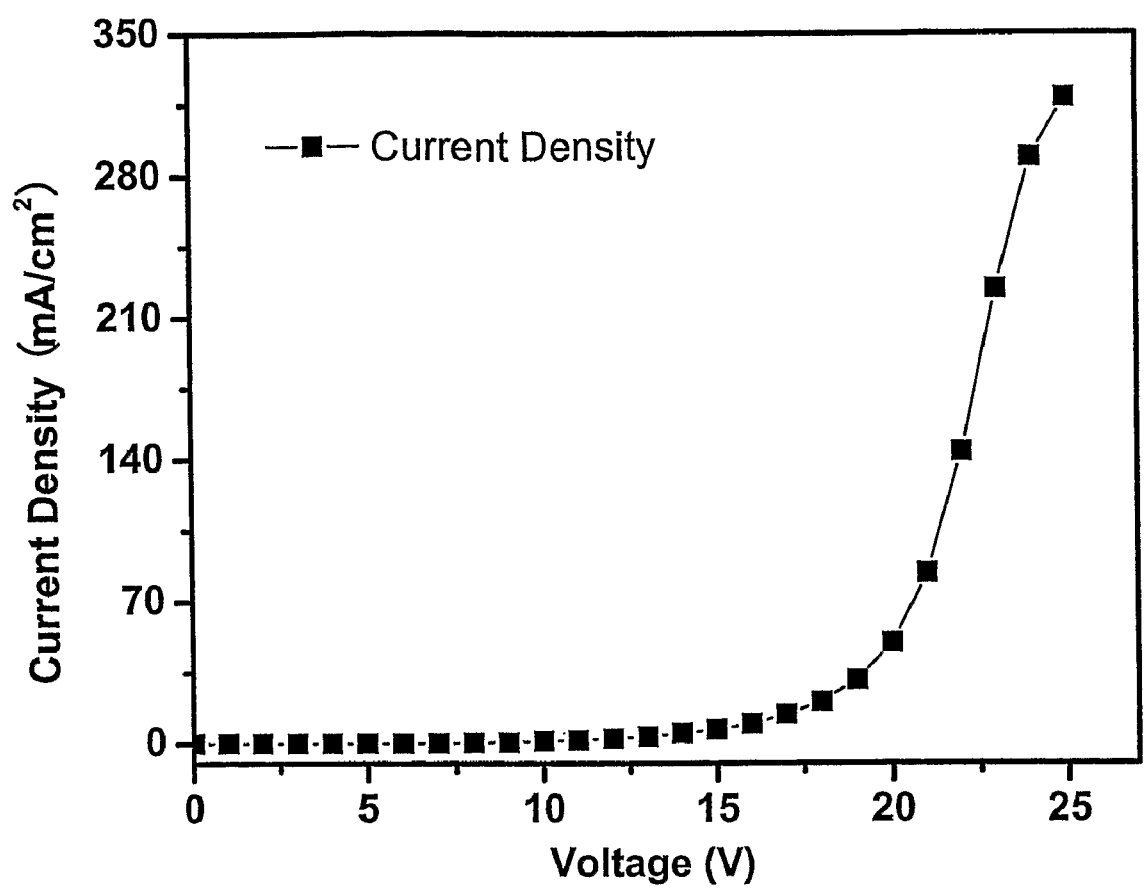
FIG. 2. The current density-voltage characteristics of the single-layer PLED, showing the current rectification properties.
Figure 3:
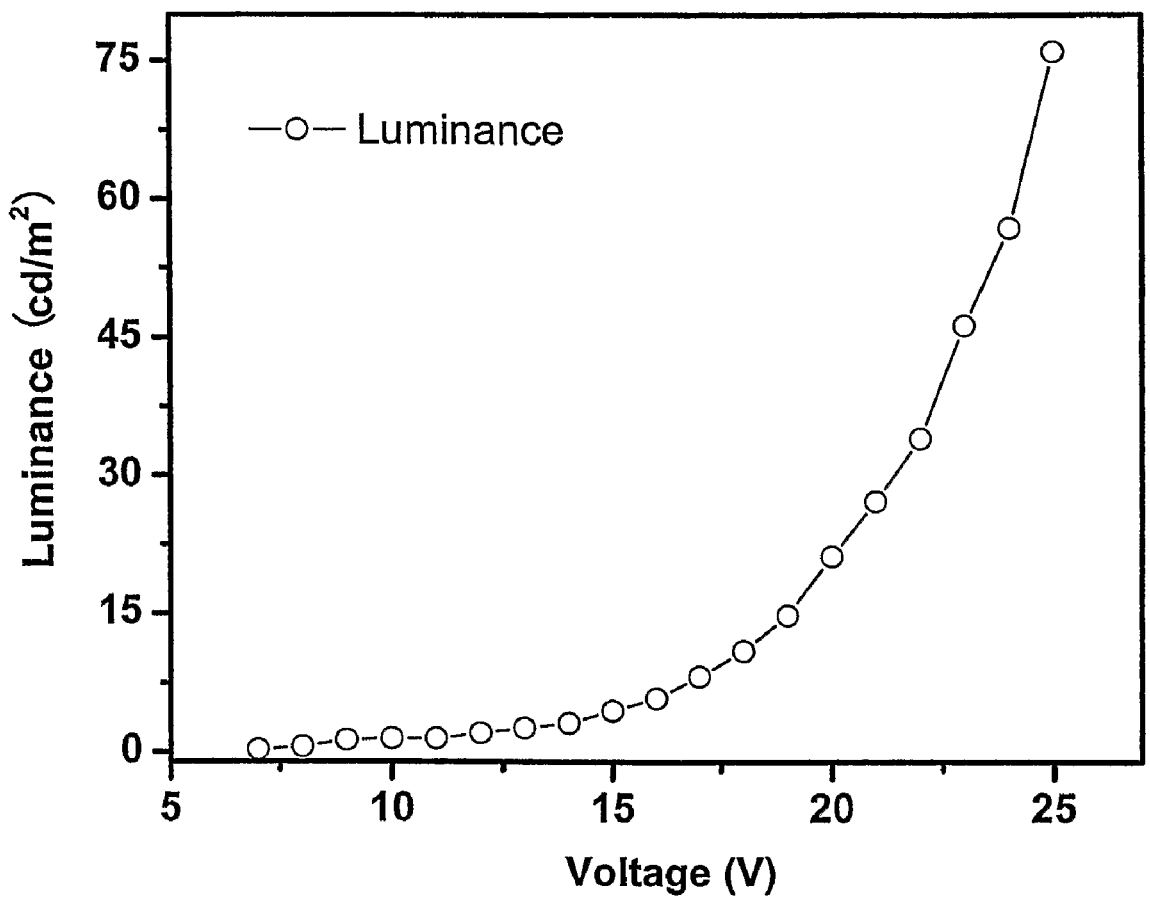
FIG. 3. The luminance-voltage characteristics of the single-layer PLED, showing the light-emitting properties.

As used in this invention, the term "rare earth" or "rare earth metal" is intended to mean the lanthanide metal or ion; the term "complex" is intended to mean a compound having at least one rare earth metal ion coordinated to at least one ligand; by "coordinated", it is meant that one atom of the functional group forms a bond with the rare earth metal; the term "ligand" is intended to mean a molecule, ion, or atom that is attached to a rare earth atom or ion; the term "polymer complex" or "copolymer complex" is intended to mean respectively a polymer or copolymer having at least one functional group(s) which is coordinated to at least one rare earth metal; the term "copolymer" refers to a polymer derived from more than one species of monomer; the term "block copolymer" refers to a copolymer made up of constituent macromolecules and wherein the adjacent blocks are constitutionally different, i.e. the adjacent blocks comprise constitutional units derived from different species of monomer, or from the same species of monomer but with a different composition or sequence distribution of constitutional units; the term "random copolymer" refers to a copolymer made up of constituent macromolecules wherein the probability of finding a given monomeric unit at any given site in the chain is independent of the nature of the adjacent units.

The present invention relates to a copolymer complex of the formula:

(I)

wherein $[A_x-[B(C)]_y-D_z]$ denotes a single unit of the copolymer complex that is repeated n times, wherein n is an integer greater than one, and wherein the single unit comprises a conjugated backbone coordinated to a complex (C) comprising rare earth metal(s), x, y and z are numbers greater than zero such that x=y+z; A is selected from a group consisting of: fluorene, carbazole, oxadiazole, triphenylamine or derivatives thereof; B is a functional ligand selected from the group consisting of: benzoic acid, 1,3-diphenylpropane-1,3-dione, 1,10-phenanthroline, 2,2-bipyridine, or derivatives thereof; and D is independently selected from a group consisting of: fluorene, carbazole, oxadiazole, triphenylamine or derivatives thereof.

The compound of formula (I) above as well as other formulae herein used may also be represented with the formula:

wherein the T—represents a terminal group. T may be any compound, group or element, for example, an organic compound comprising a single halogen group, such as bromobenzene, chlorobenzene, and the like. T is not specifically controlled for the purpose of the present invention. Accordingly, for the purpose of the present invention, T may be either present or omitted from the formulae, and the formulae will have the same meaning. Generally, T will be omitted in the formulae presented herein. As used also herein, Formula (I) refers to either the without or with T.

The copolymer complex of formula (I) as well as the intermediate copolymer complex of formula (II)

(II)

may be a random or block copolymer complex, wherein n is an integer greater than one, and wherein the single unit $[A_x-B_y-D_z]$ represents a conjugated backbone wherein: A is a group comprising at least one of fluorene, carbazole, oxadiazole, triphenylamine or derivatives thereof; B is a functional ligand selected from the group consisting of: benzoic acid, 1,3-diphenylpropane-1,3-dione, 1,10-phenanthroline, 2,2-bipyridine, and derivatives thereof; D is the same or different to A and is a group comprising at least one of fluorene, carbazole, oxadiazole, triphenylamine or derivatives thereof, and wherein x, y and z are numbers greater than zero such that x=y+z.

The copolymer complexes of formulae (I) and (II) may exhibit properties such as solubility in aqueous media and/or mechanical flexibility, as well as possess semi-conducting properties, and/or exhibit pure red, blue or green emission.

In the polymer complex of formula (I), A is one of the blocks to build up the conjugated backbone, and may act also as an energy harvesting group and/or charge transport group. Examples of compounds for use as block A are fluorene, carbazole, oxadiazole or triphenylamide group and their derivatives. In particular, fluorene and/or its derivatives may be chosen as block A since polymers of fluorene and/or derivative thereof are known as wide-bandgap, high-efficient luminescence materials.

The building block A is unique in each copolymer complex and may be represented by the formula:

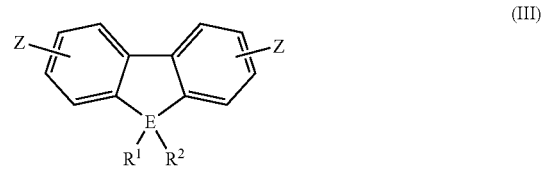
(III)

wherein $R^1$ and $R^2$ are the same or different and are linear or branched $C_{1-20}$ alkyl or alkoxy groups or at least one of $R^1$ and $R^2$ is absent, Z is a point of connection to a further block of the copolymer, E is a carbon atom (C) or a nitrogen atom (N), and when E is a nitrogen atom Z is at positions 3 and 6, and when E is a carbon atom Z is at positions 2 and 7.

For the purpose of the present invention the formulae herein shown may either include or not the letter Z, which represent the point of connection to a next or further block of the copolymer complex according to the invention. Formulae with either or without the letter Z will have the same meaning.

$R^1$ and $R^2$ may be the same or different and are linear or branched $C_{1-20}$ alkyl, or alkoxy groups. In particular, each of $R^1$ and $R^2$, independently, may be selected from the group consisting of: n-hexyl group, 2-ethylhexyl group, n-octyl group, n-decyl group, n-dodecyl group, 2-hexyldecyl group, n-octadecyl and corresponding alkoxyl groups.

A may be a fluorene group, in that case E is a carbon atom and $R^1$ is the same as $R^2$. A may also be a carbazole group, in that case E is a nitrogen atom and $R^2$ is absent. $R^1$ and $R^2$ may be introduced to the fluorene ring to improve the solubility of the polymer complexes in organic solvents, but do not affect the luminescent properties. Accordingly, the group A may be represented by the formula:

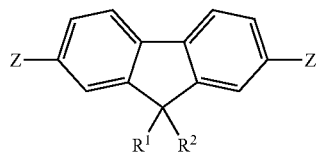

(IV)

wherein X, $R^1$ and $R^2$ are substituents at C9 atom of the ring and are as defined above.

The building block D is independently selected in each copolymer complex. It may be the same as Block A, or it may be selected from the group consisting of derivatives of oxadiazole and derivatives of triphenylamine of the following formulae:

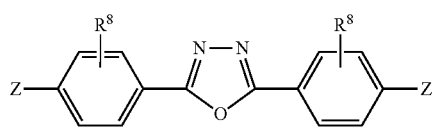

(V)

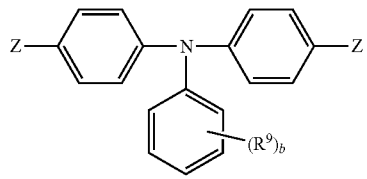

(VI)

wherein $R^8$ is independently selected from the group consisting of: hydrogen, alkyl, perfluoroalkyl, alkoxy, aryl and aryloxy groups; $R^9$ is independently selected from hydrogen, alkyl, alkoxy, carboxyalkyl or carboxyaryl, wherein $R^8$ or $R^9$ is $C_{1-20}$ and b is an integer in the range of 0 to 3. Z represents a point of connection to a next or further block of the copolymer. The alkyl or alkoxy group is linear, branching or cyclic, with carbon atoms in the range $C_{1-20}$. In one aspect of the invention, the building block D which makes up the copolymer complex is different from the building block A at each occurrence.

Another building block making up the copolymer complex is the block [B(C)]. In particular, [B(C)] represents an organic complex, wherein C may be represented by the formula:

$$M(L^1)_a(L^2)_b \quad (VII)$$

wherein M is a rare earth metal ion; $L^1$ is an enolate, carboxylate, sulfonate, alkoxide, or amide ligand; $L^2$ is a neutral ligand selected from the group consisting of: 1,10-phenanthroline (phen), 2,2-bipyridine group (bpy), 2,6-di(pyridine-3-yl)pyridine (tpy), phosphine oxide and derivatives thereof; a is an integer in the range of 2-4; and b is 0 or 2.

In one embodiment, the organic complex [B(C)] may be indicated with the formula:

$$(B)M(L^1)_a \quad (VIII)$$

wherein M is an independent rare earth ion, $L^1$ is selected from the group consisting of: enolate, carboxylate, sulfonate, alkoxide, amide ligands and derivative thereof and a is an integer in the range of 2-4.

Examples of the organic complex [B(C)] include but are not limited to:

(a)

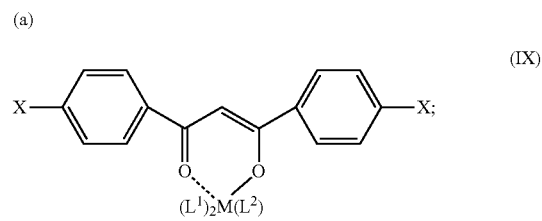

(IX)

(b)

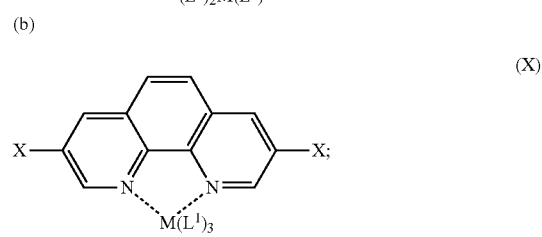

(X)

(c)

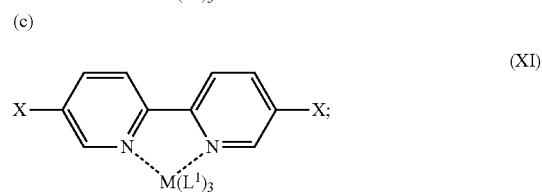

(XI)

(d)

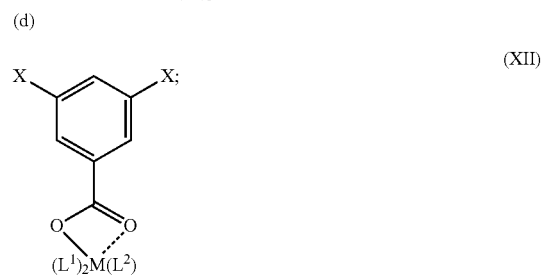

(XII)

wherein X is independently in each occurrence a halide; M is a rare earth metal ion; $L^1$ is an enolate, carboxylate, sulfonate, alkoxide, or amide ligand; $L^2$ is an independent neutral ligand selected from the group comprising 1,10-phenanthroline (phen), 2,2-bipyridine group (bpy), 2,6-di(pyridine-3-yl)pyridine (tpy), phosphine oxide and derivatives thereof.

M is a rare earth metal ion which may be selected from the group consisting of: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu), scandium (Sc) and yttrium (Y).

The emission efficiency of a rare earth complex depends strongly on the effective energy transfer from the polymer domain to the rare earth ions. This is a two-step energy transfer process involving: a) Förster energy transfer from the conjugated blocks to the ligands, and b) Dexter energy transfer from the ligands to the excited states of the rare earth ions. In order to utilize the Förster energy transfer in the polymer complex, a proper energy donor-acceptor system must be selected. It requires the overlap of the emission spectrum in the donor and the absorption spectrum in the acceptor. Since most of the rare earth complexes absorb in the region of 200-400 nm, only those polymers with emission bands that fall in the ultra-violet or blue light region may serve as a donor.

The block B may be independently selected in each polymer complex of formula (I). It may be the derivatives of benzoic acid (benzoate), 1,3-diphenylpropane-1,3-dione, 1,10-phenanthroline, or 2,2-bipyridine group of the formulae:

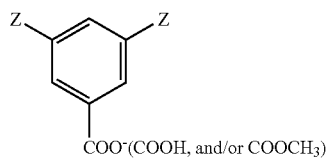
(XIII)

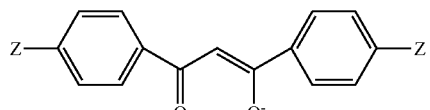
(XIV)

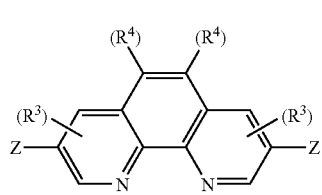
(XV)

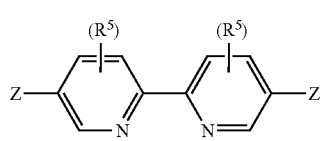
(XVI)

wherein $R^3$, $R^4$ and $R^5$ represent independently selected hydrogen atom, alkyl group, perfluoroalkyl group, alkoxy group, aryl group and aryloxy group. The alkyl group or alkoxy group may be linear, branching or cyclic, and may have about 1 to 20 carbon atoms. Examples thereof include methyl, ethyl, butyl, hexyl, octyl and their corresponding perfluoroalkyl, alkoxyl groups, etc. The aryl group or aryloxy group may have about 6 to 20 carbon atoms. Examples thereof include phenyl, alkylphenyl, naphthyl, fluorenyl and their corresponding aryloxy groups, and the like. As used herein, a substituent R may be indicated with a number n which may be placed either before (i.e. $^nR$) or after (i.e. $R^n$) the letter R and have the same meaning. For example, either $^4R$ or $R^4$ may be used and have the same meaning.

The block C is independently selected in each copolymer complex of formula (I), comprising ligands coordinated to a rare earth ion. C may be represented by Formula:

$$M(L^1)_a(L^2)_b \qquad (VII)$$

wherein M is an independently selected rare earth ion, $L^1$ is an independently selected derivative of enolate, carboxylate, sulfonate, alkoxide, or amide ligands, $L^2$ is an independently selected neutral ligand and wherein a is an integer in the range 2-4 and b is 0 or 2.

Examples of preferred M is the trivalent ion of lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu). In some cases, the trivalent ion of scandium (Sc) and yttrium (Y) is also included. In one embodiment, $Eu^{3+}$, $Tb^{3+}$, $Tm^{3+}$, $Dy^{3+}$ and $Er^{3+}$ may be used. Red, green, blue, white and infrared emissions with narrow bandwidth from the respective complexes of the $Eu^{3+}$, $Tb^{3+}$, $Tm^{3+}$, $Dy^{3+}$ and $Er^{3+}$ ions are expected since the emission from rare earth ions originates from transitions between the f levels that are well protected from environmental perturbations by the filled $5s^2$ and $5p6$ orbitals.

$L^1$ may be an enolate ligand of the formula:

(XVII)

wherein $R^6$ and $R^7$ are alike or different from each other and may be be substituted or unsubstituted alkyl, aryl, alkylaryl or heterocyclic group. Adjacent $R^6$ and/or $R^7$ groups can be joined to form five- and six-membered rings, which can be substituted, and may be N—, O—, or S-containing heterocyclic rings. Preferred $R^6$ and $R^7$ groups are selected from $C_nH_{2n+1}$, $C_nF_{2n+1}$, phenyl, thienyl, alkylphenyl, naphthyl, fluorenyl groups and their derivatives, where n is an integer in the range of 1 to 6. Examples of suitable enolate ligands are listed in Table (I):

TABLE (I)

| $R^6$ | $R^7$ | Abbreviation | Name |
|---|---|---|---|
| H₃C— | —CH₃ | acac | 2,4-pentanedionate |
| phenyl | —CH₃ | BA | 1-phenylbutane-1,3-dionate |
| phenyl | phenyl | DBM | 1,3-diphenyl-1,3-propanedionate |

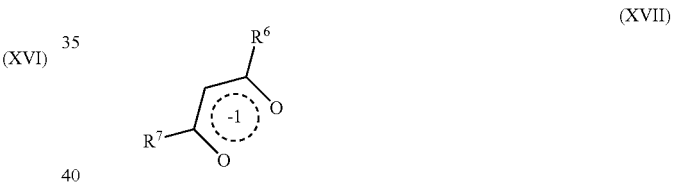

TABLE (I)-continued

| R⁶ | R⁷ | Abbreviation | Name |
|---|---|---|---|
| 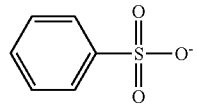 | —CF₃ | TTA | 4,4,4-trifluoro-1-(2-thienyl)-1,3-butanedionate |
| F₃C— | —CF₃ | HFA | 1,1,1,5,5,5-hexafluoropentane-2,4-dionate |
| 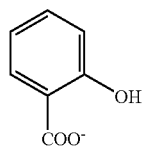 | —CF₃ | FPA | 4,4,4-trifluoro-1-phenylbutane-1,3-dionate |
| 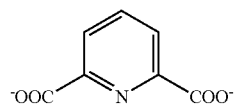 | —CF₃ | NTA | 4,4,4-trifluoro-1-(naphthalene-3-yl)butane-1,3-dionate |
| 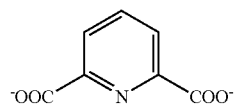 | 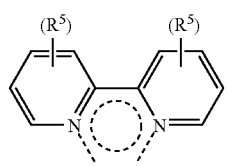 | DNM | 1-(naphthalene-2-yl)-3-(naphthalene-3-yl)propane-1,3-dionate |
| 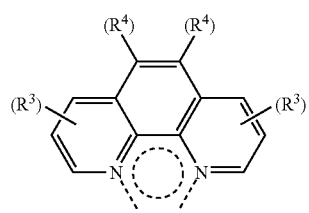 | —C₂F₅ | FIPA | 1-(9H-fluoren-2-yl)-4,4,5,5,5-pentafluoro pentane-1,3-dionate |

In order to utilize the Dexter energy transfer in the rare earth complexes, the energy levels of the singlet and triplet excitons of a ligand must lie above the corresponding levels in the rare earth. Thus, $L^1$ may also be benzenesulfonate, salicylate (sal) and pyridine-2,6-dicarboxylate (DPA) which have the following formulae (XVIII to XX), respectively.

(XVIII)

(XIX)

(XX)

The neutral ligand $L^2$ of formula (XXI) may be used as a synergic agent, which not only satisfies the coordination number of the rare earth ion, but also acts as the electron transport group. $L^2$ can be a derivative of 1,10-phenanthroline (phen) or 2,2-bipyridine group (bpy) of the formulae below:

(XXII)

(XXIII)

wherein $R^3$, $R^4$ and $R^5$ represent independently selected hydrogen atom, alkyl group, perfluoroalkyl group, alkoxy group, aryl group and aryloxy group. The alkyl group or alkoxy group may be linear, branching or cyclic, and may have about 1 to 20 carbon atoms. Examples thereof include methyl, ethyl, butyl, hexyl, octyl and their corresponding perfluoroalkyl, alkoxyl groups, etc. The aryl group or aryloxy group may have about 6 to 20 carbon atoms. Examples thereof include phenyl, alkylphenyl, naphthyl, fluorenyl and their corresponding aryloxy groups, and the like. Preferably, $R^3$, $R^4$ and $R^5$ include methyl group, phenyl group, pyridyl group and trifluoromethyl group. $L^2$ can also be a phosphine oxide of the formula:

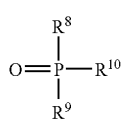

(XXIV)

wherein $R^8$, $R^9$ and $R^{10}$ are alike or different from one another. They can be phenyl, amide, alkyl, alkoxy group and their halogen-substituted derivatives. Among them, triphenylphosphine oxide (TPPO), hexamethylphosphorotriamide (HMPA), trioctylphosphine oxide (TOPO), [(diisobutylcarbamoyl)methyl]octylphenylphosphine oxide (CMPO), tributoxyphosphine oxide (TBPO) of the following formulae (XXV) to (XXIX), respectively, are preferable:

(XXV)
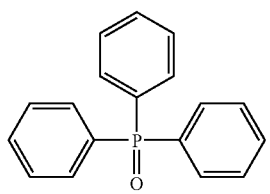

(XXVI)
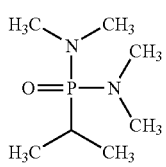

(XXVII)
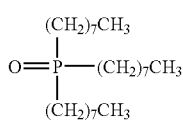

(XXVIII)
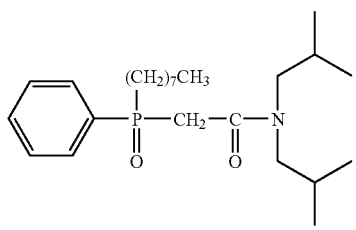

(XXIX)
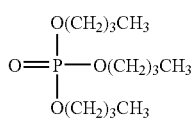

Processes for Preparing Rare Earth Metal Complexed-Monomers of Formulae (II to V)

Another aspect of this invention is directed to the synthesis of the rare earth metal complexed-monomers of the formulae of (IX) to (XII). Numerous methods are known in the art for syntheses of metal-ligand complexes.

One approach to the synthesis of the rare earth metal complexed-monomers of the formulae (II) to (V) is by a general procedure (Moeller, T. *Gmelin Handbook of Inorganic Chemistry*; Springer-Verlag: New York, 1981; vol. 39(D3), p. 65-232). The synthesis may be represented by Equation 1:

(Equation 1)
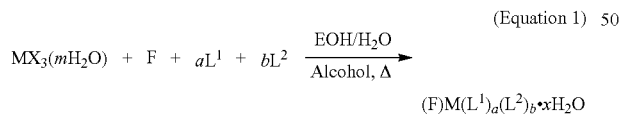

wherein M is a rare earth metal ion, X is a halide; E is an alkali metal; F is a functionalized aromatic ligand; $L^1$ is an enolate, carboxylate, sulfonate, alkoxide, amide ligands or their corresponding anions; $L^2$ is a neutral ligand; a is an integer from 2-4; b is an integer of 0 or 2; and m is an integer.

The rare earth metal complexes may be synthesized by dissolving the ligands F, $L^1$ and $L^2$ in warm alcohol such as methanol, ethanol or isopropanol, at temperatures from about 60° C. to about 70° C., followed by neutralizing the reaction mixture with an aqueous base solution, and addition of the rare earth halide solution. Preferably, 1 equivalent of rare earth halide (with or without coordinated water molecules), 1 equivalent of functionalized ligand (F), 2 equivalents or greater of the co-ligand ($L^1$) and 0 to 2 equivalents of the neutral ligand ($L^2$) are used in the synthesis.

In the present invention, M is a rare earth metal ion, X is a halide; E is an alkali metal; F is a functionalized aromatic ligand; $L^1$ is an enolate, carboxylate, sulfonate, alkoxide, amide ligands or their corresponding anions; $L^2$ is a neutral ligand; a is an integer in the range of 2-4; b is 0 or 2; m is an integer, preferably from 0 to 6 and F is selected from the group comprising 1,3-bis(4-bromophenyl)propane-1,3-dione (DBDBM), 3,5-dibromobenzoic acid (DBBA), methyl-3,5-dibromobenzonate (DBBM), 3,8-dibromo-1,10-phenanthroline (DBPhen), and 5,5'-dibromo-2,2'-bipyridine (DBBpy), represented by Formulae (XXX), (XXXI), (XXXII), (XXXIII) respectively.

(XXX)
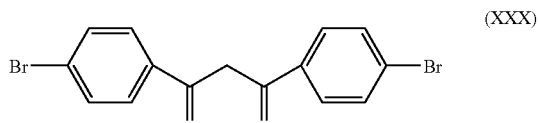
[DBDBM]

(XXXI)
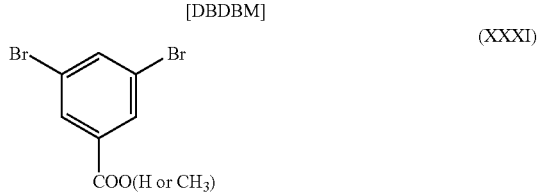
[DBBA]

(XXXII)
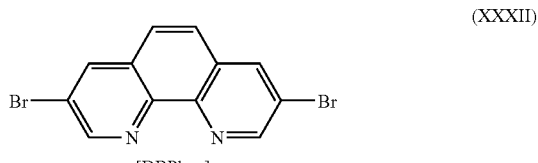
[DBPhen]

(XXXIII)
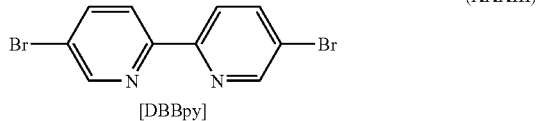
[DBBpy]

The functionalized ligands DBBA and DBBM may be purchased commercially. The ligand DBDBM may be prepared using a Claisen condensation between ethyl-4-bromobenzoate and an equivalent amount of 4'-bromoacetophenone in the presence of sodium alkoxide in dry diethyl ether. The ligand DBPhen may be synthesized by bromination of 1,10-phenanthroline (phen) with bromine. However, as phen is a typical π-deficient aromatic compound, selectivity of bromination as well as yield of the desired brominated product is typically low. In the presence of $S_2Cl_2$ and pyridine, DBPhen can be prepared in good yield. The ligand DBBpy can be prepared by direct bromination of 2,2'-bipyridine hydrobromide salt with liquid bromine in a sealed tube at high temperatures, generally about 180° C.

Using the above synthetic method, ESI-MS results indicate that most of the rare earth metal complexes synthesized contain several coordinated water molecules and multiple derivatives comprising chelated ligands. The drawback with these synthesized complexes is that the H—O vibration of the water molecule tends to quench the fluorescence intensity.

To avoid the coordination of water molecules and achieve a well-defined rare earth metal complex, the rare earth metal complexed-monomers of Formulae (IX) to (XII) can also be prepared via a novel method as represented in Equation 2:

(Equation 2)

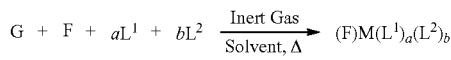

$$G + F + aL^1 + bL^2 \xrightarrow[\text{Solvent}, \Delta]{\text{Inert Gas}} (F)M(L^1)_a(L^2)_b$$

wherein G is a highly reactive rare earth metal salt and wherein M, F, $L^1$, $L^2$, a, and b are as defined in Equation 1. G is a highly reactive rare earth metal salt, represented by Formula (VI), may be synthesized from an anhydrous rare earth chloride (Bradley, *Metal Alkoxide,* 1978, Academic Press, New York).

The rare earth metal complexed-monomers of Formulae (IX) to (XII) may be synthesized using 1 equivalent of G, 1 equivalent of functionalized ligand (F), 2 equivalents or greater of the co-ligand ($L^1$) and 0 to 2 equivalents of the neutral ligand ($L^2$). The solvent system used is preferably a mix of (isopropanol and either benzene, tetrahydrofuran (THF) or N,N-dimethylformamide (DMF), with the mixture of (isopropanol and benzene) in the volume ratio of 1:1 being the most preferred All the solvents are carefully dried prior to use. The reaction is carried out at temperatures above room temperature, preferably about 60 to 70° C., and under an inert atmosphere such as argon or nitrogen of high purity (more than 99.999%).

In comparison with the general procedure in aqueous phase (Equation 1), this synthetic route (Equation 2) utilizing the highly reactive rare earth alkoxide in dry organic solvents affords the synthesis of rare earth-mixed ligand complexes without water molecules coordinated to the complex.

Process for Preparing the Copolymer Complex of Formula (I)

The present invention relates also to a method of producing a copolymer complex of Formula (I), comprising synthesizing a conjugated backbone [$A_x$-$B_y$-$D_z$], and post-chelation of the backbone to a rare earth complex C comprising a rare earth ion and co-ligands. The conjugated backbone may be synthesized according to any technique known in the art. For example, by reaction of a dihalide with a diboronate or diboronic acid in a Suzuki reaction. The diboronate or diboronic acid may be a derivative of 9,9-disubstituted fluorene or 9-substituted carbazole. The dihalide may be a derivative of 1,10-phenanthroline, 2,2-bipyridine, 1,3,4-oxadiazole, triphenylamine, 9,9-disubstituted fluorene and 9-substituted carbazole. The Suzuki reaction may be modified by reducing the concentration of the base and by adding a phase transfer catalyst (PTC).

An alternative synthetic route for synthesis of the conjugated backbone involves a tetrazole condensation reaction comprising reacting a ditetrazole derivative of a 9,9-disubstituted fluorene or a 9-substituted carbazole and a diacyl chloride derivative of 2,2'-bipyridine or 1,10-phenanthroline.

Post-chelation, to form the polymer complex, comprises a reaction between the conjugated backbone and the rare earth complex C, wherein the coordination number of the rare earth ion may be satisfied by neutral water molecules. The post-chelation may also comprise a reaction between the conjugated backbone and the rare earth complex C in a mixed solvent of alcohol and water, in the presence of base. Examples of the co-ligand may be a derivative of β-diketone, benzoic acid, benzenesulfonic acid, salicylic acid, or pyridine-2,6-dicarboxylic acid. In another embodiment, the post-chelation comprises a reaction between the conjugated backbone, the co-ligands and a reactive rare earth metal salt, in non-aqueous solvents. Examples of the rare earth metal salt include but are not limited to rare earth metal isopropoxides which are stable in a mixed solvent of isopropanol and benzene.

Another route for producing a copolymer complex of Formula (I) comprises formation of an organic complex [B(C)] and further reacting the organic complex to A and D to form the copolymer complex. The method comprises reacting a rare earth ion with a dihalogen-substituted ligand in aqueous alcohol at pH from about 5-8, to form the rare earth complex C. In another embodiment, the method comprises reaction of a reactive rare earth metal triisopropoxide with a dihalogen-substituted ligand in non-aqueous phase, to form an organic complex [B(C)].

The copolymer complexes produced by the methods of this invention retain desirable properties such as solubility in aqueous media, mechanical flexibility, semi-conductor properties and which have pure red, blue or green emission.

Example of Process for Preparing the Copolymer Complex of Formula (I)

Copolymer complexes may be prepared by any process suitable for the formation of C—C bond between aromatic rings of monomers to form a conjugated backbone, such as by Yamamoto (Ni catalyzed), Grignard (Mg catalyzed), Stille (Sn catalyzed), Suzuki (Pd catalyzed) and $FeCl_3$-catalyzed reactions.

One method (Method A) is the Suzuki reaction, which is the condensation reaction of an aromatic boronate and a bromide, reported by Miyaua and Suzuki in *Chem. Rev.,* 95, 2457-2483 (1995), is most preferable, since this reaction has been found to be less sensitive to steric hindrance and tolerant to a variety of functional groups, and it can be carried out under mild reaction conditions with fewer side reactions and higher conversions.

Another method (Method B) involves a condensation reaction between tetrazole and carboxylic chloride, reported in *Macromolecules,* 35, 3474-3483 (2002) in the so-called "Tetrazole route", and the post-chelation with the rare earth metal complex.

The Suzuki reaction can be applied to preparing high molecular weight polymers and copolymers. To prepare the copolymer complexes of the Formula (I), a dihalide with the Formulae (IV), (XXXVI-XXXXI) listed in Table (II), and a diboronic acid or diboronate of fluorene or carbazole derivative corresponding to Formulae (XXXXIII)~(XXXXIV), is first synthesized.

TABLE (II)

| No. | Formula | No. | Formula |
|---|---|---|---|
| (IV) | | (XXXIV) | |

TABLE (II)-continued

| No. | Formula | No. | Formula |
|---|---|---|---|
| (XXXV) | | (XXXVI) | |
| (XXXVII) | | (XXXVIII) | |
| (XXXIX) | | | |
| (XXXX) | | | |

In Formulae of (IV), (XXXIV) to (XXXX), X is an independent halogen group. $R^1$ to $R^5$ are as defined in Formulae (X), (XI) and (XII). $R^8$, $R^9$ and b are as defined in Formulae (XXIV) and (VII). In Formula (XXXX), the 1,3,4-oxadiazole group can be connected to the 4,4'- or 5,5'-positions of the 2,2'-bipyridine group. The 2,7-dihalo-9,9-disubstituted fluorenes of Formula (VII) may be prepared by reacting a 2,7-dihalofluorene with at least 2 equivalents of $R^1X$ in the presence of a phase transfer catalyst and an alkali metal hydroxide (as described in U.S. Pat. Nos. 6,169,163 and 5,962,631). It can also be prepared by a reaction of fluorene with at least 2 equivalents of $R^1X$ using n-butyllithium, followed by halogenation of 9,9-disubstituted fluorene using excess halogen (reported by Fukuda, *J. Polym. Sci. A: Polym. Chem.*, 31, 2465, (1993)). The 2,7 (or 3,6)-dihalo-9-substituted carbazoles of Formula (XXXIV) may be prepared by reacting a 2,7 (or 3,6)-dihalocarbazole with at least one equivalent of $R^1X$ in the presence of a phase transfer catalyst and an alkali metal hydroxide. The 3,8-dibromo-1,10-phenanthroline derivatives of the Formula (XXXV) can be synthesized by bromination reaction in the presence of $S_2Cl_2$ and pyridine. The 5,5'-dibromo-2,2'-bipyridine derivatives of the formula (XXXVI) can be prepared by direct bromination of 2,2'-bipyridine hydrobromide salt with liquid bromine in a sealed tube at high temperature (180° C.). The dihalide derivatives of 1,3,4-oxadiazole of the Formula (XXXVII) can be prepared by the reaction of the corresponding benzoic hydrazide and benzoic chloride in dry pyridine followed by cyclization in the presence of $SOCl_2$ or polyphosphoric acid. The dibromo-triphenylamine derivative of the Formula (XXXVIII) can be synthesized by bromination of the corresponding triphenylamine with N-bromosuccinimide. The 5,5'(or 4,4')-bis[2-(4-bromophenyl)-1,3,4-oxadiazoyl]-2,2'-bipyridine of the formula (XXXIX) can be synthesized by the reaction between the corresponding 2,2'-bipyridinedicarbonyl chlorides and 1-bromo-4-tetrazoyl-benzene in dry pyridine.

The diboronic acid and diboronate of fluorene or carbazole derivatives have the formulae (XXXXI) to (XXXXII):

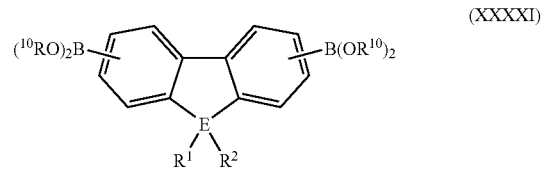

(XXXXI)

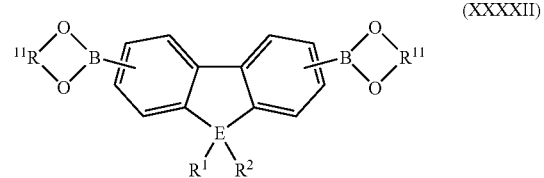

(XXXXII)

wherein, E is carbon atom (C) or nitrogen atom (N). $R^1$ and $R^2$ are as defined in Formula (II). $R^{10}$ (equivalent to the format of $^{10}R$) is an independent hydrogen group or a $C_{1-10}$ alkyl group. $R^{11}$ (equivalent to the format of $^{11}R$) is an independent $C_{2-10}$ alkylene (straight or branched) group. When E is a carbon atom, the boronic or boronate group is connected to the 2 and 7 position of fluorene group. When E is a nitrogen atom, the boronic or boronate group is connected to the (2 and 7), or (3 and 6) position of carbazole group. The 2,7-diboronate or -diboronic acid fluorene derivatives of the Formula (XXXXI) may be prepared by the method described by Yu et al. in *Chem. Comm.*, 1837 (1999). The 2,7-dihalo-fluorene of the Formula (IV) (or (XXXIV)) reacts with at least two equivalents of magnesium to form a bifunctional Grignard reagent, which is converted to the corresponding diboronate of the Formula (XXXXI) by reaction with 2 equivalents of (R⁸O)₃B at a low temperature (preferred from −80° C. to room temperature). The resulting diboronate can be further converted to the corresponding diboronic acid by a hydrolysis reaction catalysed by diluted acid solution. Esterification of the diboronic acid with an alkylenediol, such as ethylene glycol or 1,3-propanediol, gives the corresponding di(cyclic) boronate of the Formula (XXXXII). The 3,6 (or 2,7)-diboronate or -diboronic acid carbazole derivatives of the Formula (XXXXI) or (XXXXII) may be prepared by the reaction of 3,6 (or 2,7)-dihalo-carbazole of the Formula (IV) (or (XXXIV)) with at least two equivalents of n-butyllithium in THF at −78° C.

The process of Method (A) for preparing the functional copolymer ligand of the Formula (XXXXIII) is illustrated in the Equation 1:

(Equation 1)

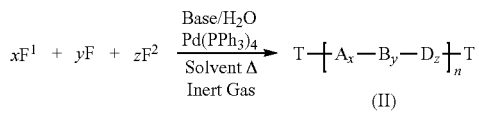

wherein x=y+z; A, B, C, D and T are defined in Formula (I). F¹ is a diboronic acid or diboronate of fluorene derivative corresponding to Formulae (XX) or (XXXII). F² may be the same as F¹, or a derivative of oxadiazole or triphenylamine of the formulae (XXXVII) or (XXXVIII), respectively. F is a functionalized ligand of the Formula (XXXIX or (XXXX). In some cases, the functional ligand F and the charge transport monomer F¹ can be combined as in the Formulae of (XVIII) and (XIX).

To prepare the copolymer ligand, F¹ is reacted with an equimolar amount of a mixture of F and F² under the catalytic action of a palladium complex, Pd(PPh₃)₄ or tetrakis(triphenylphosphine)palladium(0). Typically, the copolymerization is conducted at about 70° C. to 120° C., in an aromatic hydrocarbon solvent, such as toluene. Other solvents, such as dimethylformamide (DMF) and tetrahydrofuran (THF), can also be used alone, or as mixtures with aromatic hydrocarbons. An aqueous base, preferably sodium (or potassium) carbonate or bicarbonate, is used as the HX scavenger. It is preferable to carry out the process under an inert atmosphere, such as argon or nitrogen with high purity (>99.9%), since the catalyst is very sensitive to oxidation. Depending on the reactivities of the reactants, the polymerization reaction may take 2 to 100 hours.

To prepare the copolymer complexes of the Formula (I) by Method (B), a ditetrazole of fluorene or carbazole derivative corresponding to Formulae (XXXXIV) and (XXXXV), and a diacyl chloride of 2,2'-bipyridine or 1,10-phenanthroline derivative corresponding to formulae (XXXXVI) to (XXXXVII), must be synthesized first.

(XXXXIV)

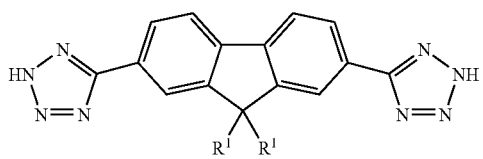

(XXXXV)

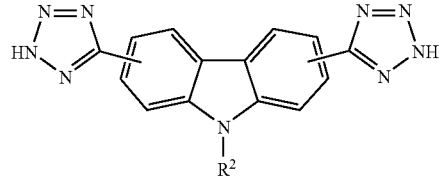

(XXXXVI)

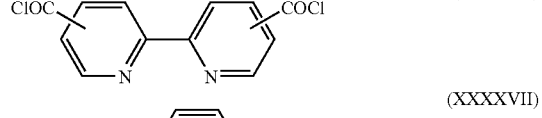

(XXXXVII)

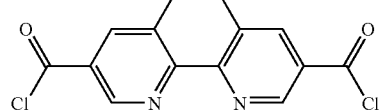

wherein R¹ and R² are as defined in Formula (II). The 2,7-ditetrazole-9,9-disubstituted-fluorenes of Formula (XXXXIV) can be prepared by the reaction of 2,7-dicyano-9,9-dihexylfluorene with NaN₃ in the presence of (n-Bu)₃SnCl. The 2,7 (or 3,6)-ditetrazole-9-substituted-carbazoles of Formula (XXXXV) can be similarly synthesized. The 2,2'-bipyridine-5,5' (or 4,4')-dicarbonyl dichloride, 1,10-phenanthroline-3,8-dicarbonyl dichloride of Formulae (XXXXVI) and (XXXXVII), respectively, can be prepared by the reaction of the corresponding dicarboxy species with excess thionyl chloride (SOCl₂).

The process of Method (B) for preparing the functional copolymer ligand of Formula (XXVII) is illustrated in Equations 2:

(Equation 2)

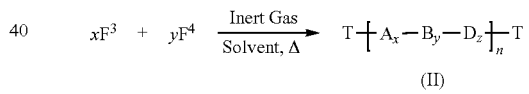

wherein x=y=z; A, B, D and T are defined in Formula (I), F³ is a ditetrazole of fluorene or carbazole derivative corresponding to Formulae of (XXXXIV) and (XXXXV) and F⁴ is a diacyl chloride of 2,2'-bipyridine or 1,10-phenanthroline derivative corresponding to formulae (XXXXVI) to (XXXXVII). This reaction exhibits several advantages in comparison to the other reactions. The most important advantages are that side reactions are minimized and high yields are possible. Secondly, an alternating copolymer with well-defined structure can be obtained in a high yield. Thirdly, the molecular mass was sufficiently high, and compared favorably with those obtained from well-developed polycondensation reactions. Typically, F³ is reacted with an equimolar amount of F⁴ in an anhydrous solvent, preferably pyridine or triethylamine, at the refluxing temperature. It is preferable to perform such process under an inert atmosphere, such as argon or nitrogen with high purity (>99.9%), since the reactant is moisture sensitive. The polymerization reaction may take 2 to 24 hours. The resulting polymer or oligomer was recovered from the reaction solution by precipitation in methanol and collection by filtration.

There are at least two methods, viz., the "direct synthesis" and "post-chelation", via the Suzuki reaction for preparing the copolymer complexes of the Formula (I). As used herein, the term "direct synthesis" is intended to mean the synthesis of a copolymer complex by condensation copolymerization of a fluorene monomer directly with a rare earth metal complexed-monomer. In the "post-chelation" process, a functional copolymer of Formula (II) is synthesized initially, and then, together with the other ligands, chelates a rare earth ion to form the copolymer complex.

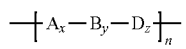
(II)

wherein x=y+z; A, B, D and T are as defined in Formula (I).

The process of direct synthesis is illustrated in Equation 3:

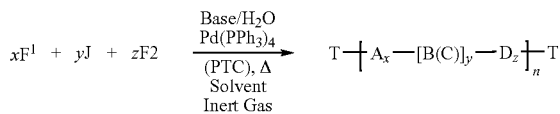
(Equation 3)

wherein x=y+z; $F^1$ is a diboronic acid or diboronate of fluorene derivative corresponding to the Formulae (XXXXI) and (XXXXII); $F^2$ is a dihalide of the fluorene derivative of Formula (IV); J is a rare earth metal complexed-monomer of the Formulae (IX to XII); and A, B, C, D and T are as defined in Formula (I).

To prepare the copolymer complex, $F^1$ is reacted with an equimolar amount of J or a mixture of J and $F^2$ under the catalystic action of a palladium complex, $Pd(PPh_3)_4$ or tetrakis(triphenylphosphine)palladium(0). Typically, the copolymerization is conducted at about 70° C. to 120° C., in an aromatic hydrocarbon solvent, such as toluene. Other solvents, such as dimethylformamide (DMF) and tetrahydrofuran (THF), can also be used alone, or in mixtures with, an aromatic hydrocarbon. An aqueous base, preferably sodium (or potassium) carbonate or bicarbonate, is used as the HX scavenger. It is preferable to perform such process under an inert atmosphere, such as argon or nitrogen of high purity (>99.999%), since the catalyst is very sensitive to oxidation. Depending on the reactivities of the reactants, a polymerization reaction may take 2 to 100 hours.

Under the above conditions of Suzuki reaction, decomposition of the rare earth metal complexed-monomer occurs extensively, as indicated by the appearance of yellow precipitates in 4-7 h after the reaction is initiated. It is probably due the highly basic environment of the normal Suzuki reaction. In the presence of a phase-transfer catalyst (PTC), the coupling reaction can be carried out under relatively mild conditions. Preferred PTCs are quaternary ammonium salts, quaternary phosphonium salts, polyethylene glycols and crown ethers, with the quaternary ammonium salts being the most preferred among them. This modification can reduce the extent of decomposition of the rare earth metal complexed-monomer and thus afford higher yield of a copolymer complex with higher molecule weight.

There are at least three methods for the post-chelation of the copolymer ligand of Formulae (XXXXIII) or (II) with rare earth ions to form the copolymer complexes of the present invention. The processes for these three methods are illustrated in Equations 3 to 5:

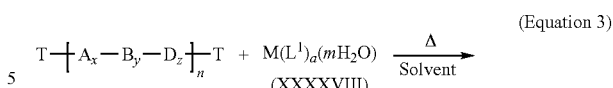
(Equation 3)

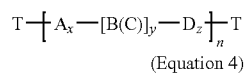
(Equation 4)

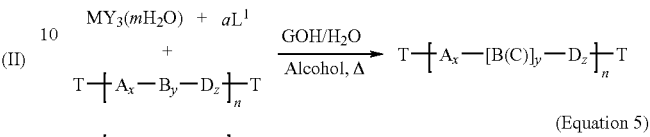
(Equation 5)

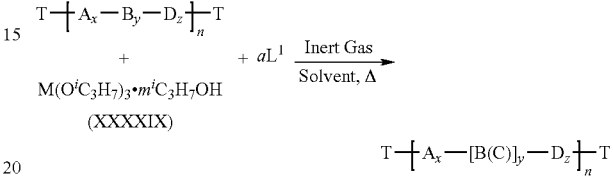

wherein A, B, C, D, T, a, and $L^1$ are defined in Formula (I). $MY_3$ is a trivalent rare earth salt which may coordinate with several water molecules, wherein M is as defined in Formula (I). Y is a halogen ion, nitrate ion, or any other form of the counter ion. G is an alkali metal and m is an integer in the range 0 to 6 (or higher).

In the first post-chelation method illustrated in Equation 3, the copolymer ligand of Formula (II) reacts with a rare earth complex of Formula (XXXXVIII), in which the coordination number of the rare earth ion is not satisfied by a neutral ligand but by water molecules, in a suitable solvent. Preferred solvents are those which can dissolve both the copolymer ligand and the rare earth complex. Among them tetrahydrofuran (THF), toluene, N,N-dimethylformamide (DMF) and dimethylsulfoxide (DMSO) are preferred. Preferred reaction temperature is between 60-70° C. The rare earth complex of Formula (XXXXVIII) can be synthesized by the common method as described in T. Moeller, *Gmelin Handbook of Inorganic Chemistry*, Vol. 39(D3), Springer-Verlag, New York, (1981).

In the second post-chelation method illustrated in Equation 4, the copolymer ligand of Formula (XXXXIII) or (II), together with other ligands ($L^1$), react with the rare earth ion in a mixed solvent of alcohol and water and in the presence of a base to adjust the pH. Preferably, 1 equivalent of rare earth halide (with or without coordinated water molecules), 1 or more equivalents of the copolymer ligand, and 3 equivalents or greater of the co-ligand ($L^1$) are used. Preferred alkali metal hydroxides are sodium hydroxide and potassium hydroxide. Preferred alcohols are methanol, ethanol, and isopropanol, with ethanol being the most preferable. Preferred reaction temperature is 60~70° C.

In order to avoid the coordination of water molecules, the post-chelation can also be carried out in non-aqueous solvents, as shown in Equation 2. Preferably, 1 equivalent of a highly reactive rare earth metal salt of Formula (XXXXIX), which can be synthesized from an anhydrous rare earth chloride (Bradley, *Metal Alkoxide*, Academic Press, New York, (1978)), reacts with 1 or more equivalents of the copolymer ligand of Formula (XXXXIII) or (II), and 3 equivalents or greater of the co-ligand ($L^1$). Preferred solvent system is a mix-solvent of isopropanol, benzene and tetrahydrofuran (THF) or N,N-dimethylformamide (DMF), with isopropanol and benzene in the volume ratio of 1:1 being the most preferable. All the solvents are carefully dried prior to use. Preferred reaction temperature is between 60~70° C. The reaction is highly sensitive to moisture. Thus it must be carried out under an inert atmosphere. Preferred inert gas is argon or nitrogen of high purity (more than 99.9%).

In the post-chelation process, an excess amount of the rare earth ions and co-ligands ($L^1$) can be used to achieve as complete a conversion as possible of block B in the copolymer ligand, corresponding to Formula (XXXXIII) or (II), to a rare earth metal complexes and to reduce the extent of chain crosslinking caused by the complex formation between different polymer chains.

The process of post-chelation may be illustrated by Equations 4-6:

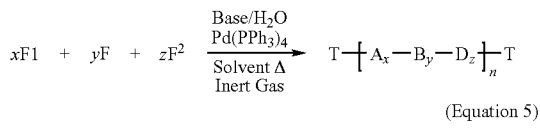

(Equation 4)

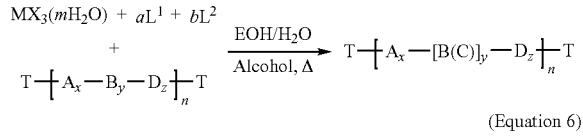

(Equation 5)

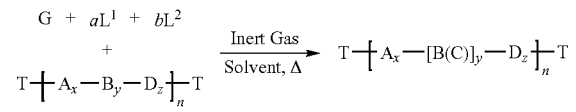

(Equation 6)

wherein x=y+z; $F^1$ and $F^2$ are as defined in Equation 3; F is a functionalized ligand of the Formula (XXXXVI), (XXXX-VII), (II), or (XXXXVIII); M is a rare earth ion as defined in Formula (VII); G is a highly reactive rare earth salt; E, X, $L^1$, $L^2$, a, b and m are as defined in Equation 1; and A, B, C, D and T are as defined in Formula (I).

A functional copolymer of Formula (XXXXX) can be prepared directly or indirectly by normal Suzuki reaction as illustrated in Equation 4. It is possible to control the sequencing of the monomeric units in the resulting copolymer by controlling the order and composition of monomer feeds in the Suzuki reaction. The functional copolymer, together with other ligands, further chelates to a rare earth ion, either by the general method represented by Equation 1 or by the non-aqueous method represented in Equation 2, to form a copolymer complex of the Formula (I). In the post-chelation process, a large excess of rare earth ions and ligands may be used to achieve as complete a conversion as possible of block B in the copolymer corresponding to Formula (XXXXX) to rare earth metal complexes and to reduce the extent of chain crosslinking caused by the complexes formation between different polymer chains.

Films Prepared from the Copolymer Complexes

Another aspect of the invention is the preparation of films formed from the copolymer complexes of this invention. Films may be prepared from the copolymer complexes and/or the organic rare earth metal complexes of the present invention.

Such films may be used in polymer light-emitting diodes (PLEDs) and other photonic or electronic devices. The thickness of the film may be varied as required. The thickness may range from about 0.01 to 200 microns. Where the films are used in polymer light-emitting diodes, the thickness of the layer formed may vary from about 0.05 to about 2 microns. The films may be prepared by means well known in the art such as spin-coating, spray-coating, dip-coating, roller-coating and ink-jet printing. The films are prepared on a suitable substrate, such as ITO glass, waveguide, silicon, depending on the device application. The process comprises dissolution of the copolymer complexes of this invention in a common organic solvent, such as toluene, chloroform and xylene. The concentration of the solution is dependent upon the boiling temperature of the solvent and the molecular weight of the copolymer complex used. Preferably, the solution contains from about 0.5 to about 5.0 weight percent of the copolymer complex. This composition is then applied to the appropriate substrate by the desired method and the solvent is allowed to evaporate. Residual solvent may be removed under vacuum and/or by heat. The films are preferably homogeneous and uniform in thickness, and free of pinholes and defects.

Another aspect of the invention relates to polymeric materials fabricated from copolymer complexes of the present invention.

Polymer Light-Emitting Diodes (PLED) Based on the Copolymer Complex

Another aspect of the invention relates to electroluminescent (EL) devices comprising the copolymer complexes of the present invention. A polymer EL device typically consists of a polymer film sandwiched between an anode and a cathode such that when a positive bias is applied to the device, holes are injected into the polymer film from the anode, and electrons are injected into the polymer film from the cathode. The combination of a hole and an electron may give rise to an exciton which may undergo radiative decay to the ground state by liberating a photon.

Such devices may include a polymer light-emitting device which comprises at least a light-emitting layer between a pair of electrodes composed of an anode and a cathode, wherein at least one electrode is transparent or semi-transparent; and wherein the light-emitting layer comprises a copolymer complex of the present invention. Another example is an organic light-emitting device which comprises at least a light-emitting layer between a pair of electrodes comprising an anode and a cathode, wherein the light emitting layer is transparent and comprises a polymeric material of the present invention.

The light-emitting device may comprise a light-emitting layer which contains a europium or samarium complex, wherein pure red emission occurs and which has a linewidth of less than 15 nm. In another embodiment, the light-emitting device may comprise a light-emitting layer which contains a terbium complex, wherein pure green emission occurs, and which has a linewidth of less than 20 nm. In another embodiment, the light-emitting device comprises a light-emitting layer which contains a thulium complex and wherein pure blue emission occurs.

The light-emitting device may also comprise a light-emitting layer which contains an erbium, neodymium, or holmium complex. The light-emitting device may also comprise a light-emitting layer which has infrared emission.

In the present invention, it is preferable that an anode is transparent or semitransparent, and as the material of this anode, electron conductive metal oxide films, such as indium oxide, tin oxide, zinc oxide, and the like are used. Specifically, films of a mixed oxide of tin and indium (ITO) are of the most preferable. ITO is deposited on a transparent substrate such as glass or plastic so that the light emitted by the polymer film may be observed. Preferred materials of a cathode used in the PLED of the present invention are the metals or alloys that having lower work function. Examples are aluminum, barium, calcium, magnesium, potassium, lithium, sodium, rubidium, strontium, and the like, or alloys comprising two of more of them, or alloys comprising one or more of them with one or more of gold, silver, platinum, copper, titanium, nickel, tungsten, indium, tin, and the like. Among them, barium, calcium, aluminum and magnesium-silver alloy, are of the most preferable. The film of a cathode can be fabricated by a vacuum vapour deposition method, sputtering method or lamination method. The film thickness of a cathode can be appropriately selected in view of electric conductivity and durability, preferably from 20 nm to 1 µm. An encapsulation layer with materials selected from polymer, metal oxide, metal fluoride, and the like is preferred. It is preferable to provide a protective layer and/or a protective cover for protection of the device from external damages. As for the protective layer, a polymer, metal oxide, metal fluoride, and the like can be used. As the cover layer, a glass plate, a plastic plate, a stainless steel plate, and the like can be used. If an inert gas, such as argon and nitrogen with high purity (>99.999%), is sealed in the covered device, it is possible to prevent oxidation of a cathode. Further more, by placing a desiccant, such as calcium chloride, magnesium sulphate, barium oxide, and the like, in the covered device, it is easy to suppress the damage of a device by moisture incorporated during the production process.

Except for the single layer PLED as described above (configuration (a) below), in order to further enhance the performance of a PLED, multi-layer EL devices, with at least one layer of which is derived from the polymer complexes of the invention, can also be fabricated. Preferred configurations of the multi-layer EL devices are described below in detail.

In order to balance the charge transport, a hole-transporting layer (HTL) can be disposed between an anode and a light-emitting layer (EML), and/or a electron transporting layer (ETL) can be disposed between a cathode and the EML. The preferable configurations are shown below:

(a) anode/EML/cathode
(b) anode/HTL/EML/cathode
(c) anode/EML/ETL/cathode
(d) anode/HTL/EML/ETL/cathode wherein and hereafter, the same, "/" indicates adjacent lamination of layers. The EML is a film of the copolymer complexes of Formula (I) and other related compounds of this invention. Preferable hole transporting materials are polymers or organic compounds, such as polyvinylcarbazole, polyaniline, polysilane, arylamine, triphenyldiamine or derivatives thereof. Specific examples of the hole transporting material include those described in JP Pat. No. 63-70257, 2-135359, 2-209988 and 3-152184. As the electron transporting materials, known organic compounds, such as the derivatives of oxidiazole, anthraquinone, benzoquinone and fluorenone, or metal complexes of 8-hydroxyquinoline, azomethine or derivatives thereof, or polymers, such as polyquinoline, polyquinoxaline, polyfluorene and the like, can be used. Specifically, the electron transporting materials are described in JP Pat. No. 63-175860, 2-135361 and 3-37992.

Alternately, the hole transporting material and/or the electron transporting material can also be mixed with the copolymer complexes of this invention and form one or more layers. Typical device configurations of the composite films are shown below:

(e) anode/HTL:EML/ETL/cathode
(f) anode/HTL/EML:ETL/cathode
(g) anode/HTL:EML:ETL/cathode wherein, ":" indicates hybridization of the functional materials of HTL, EML and/or ETL.

For enhancing adherence to an electrode and improving charge injection from an electrode, a charge injecting layer (CIL, hole injecting or electron injecting) having a thickness of 10 to 50 nm can be inserted into the interface of an electrode and, a charge transporting layer (HTL or ETL) or light-emitting layer. The CIL is a layer containing a conducting polymer, the electrical conductivity of which is preferably in the range of $10^{-5}$ to $10^3$ S/cm or less. For minimizing the leakage current between the light emitting pixels, the preferred conductivity of CIL is between $10^{-5}$ to $10^1$ S/cm. The CIL material which is disposed between the anode and HTL must have an ionization potential between those of the anode material and HTL material. The CIL material which is disposed between cathode and ETL must have an electron affinity between those of the cathode material and ETL material. The materials used for CIL may be selected in conjunction with the materials of electrode and adjacent layers. Thus, the materials used for CIL are preferentially selected from conducting polymers, such as polyaniline, polythiophene, polypyrrole, poly(phenylene vinylene), poly(thienylene vinylene) and their derivatives. To provide the electric conductivity required, a suitable amount of ions are doped into the conducting polymer. An anion, such as polystyrene sulfonate ion, alkylbenzene sulfonate ion and the like, may be used in the hole injecting layer. A cation, such as lithium ion, sodium ion, potassium ion, tetrabutyl ammonium ion and the like, may be used in the electron injecting layer. Representative device configurations with CIL layers are shown below:

(h) anode/CIL/EML/CIL/cathode
(i) anode/CIL/HTL/EML/ETL/cathode
(j) anode/HTL/EML/ETL/CIL/cathode
(k) anode/CIL/HTL/EML/ETL/CIL/cathode Besides the CIL, an insulating layer (ISL) having a thickness of 2 nm or less may also be provided adjacent to an electrode for enhancing the adherence of the interface and for, preventing mixing and the like. Such a thin buffer layer may also be inserted into the interface of an electrode and the charge transporting or light-emitting layer. Specifically, the following configurations (l) to (o) are preferred:

(l) anode/ISL/EML/ISL/cathode
(m) anode/HTL/EML/ETL/ISL/cathode
(n) anode/ISL/HTL/EML/ETL/cathode
(o) anode/ISL/HTL/EML/ETL/ISL/cathode The materials of ISL may be metal fluoride, metal oxide, metal phthalocyanine and the like. Among them, lithium fluoride, aluminum oxide and copper phthalocyanine are of the most preferable.

The order and number of layers laminated and the thickness of each layer can be appropriately tuned in accordance with the performance, such as the turn-on voltage, brightness, efficiency, lifetime and other parameters, of a light-emitting device. The method for forming these functional layers is not restrictive. It can involve thermal evaporation, vacuum vapour deposition, sputtering deposition, spin-coating, scroll-coating, dip-coating, screen printing, offset printing, inkjet printing, and the like.

Utilizing the polymer light-emitting diodes described above, and in conjunction with the formation of a pattern and micropattern by a specified method, such as shadow-mask or etching, and by the introduction of independent on/off electrodes, it is possible to obtain display devices which can display digits, letters, images and the like. The polymer light-emitting diodes may also be used in forming dot matrix displays which comprise the light-emitting devices of the present invention. By forming a dot matrix device driven by a passive driver, or by an active driver in combination with TFT, it can be used as a display in a computer, television, and the like. Furthermore, the light-emitting device can also be used directly as a flat light source, for example in the back-light of a liquid crystal display, or as a flat light source for illumination. The light-emitting devices may also be applied in segment displays.

The polymer light-emitting diodes may also be applied in a field effect transistor wherein the transistor comprises a semiconductor layer adjacent to one surface of an insulator layer, two electrodes wherein a first electrode acts as a source and a second electrode acts as a drain and wherein the two electrodes are attached to the semiconductor layer, a third electrode which acts as a gate and is positioned adjacent to another surface of the insulator layer and wherein the semiconductor layer comprises a copolymer complex of the present invention.

Other applications which comprise a material made from a copolymer complex of the present invention include an optical fiber amplifier wherein the copolymer contains an erbium, neodymium, or praseodymium complex, a photonic laser wherein the polymeric material contains a neodymium complex and an electro-optical modulator.

Having now generally described the invention, the following examples are provided by way of illustration and are not intended to be limiting of the present invention.

EXAMPLES

The invention can be better understood by reference to the following specific examples. These examples are provided to illustrate the invention and the manner in which it may be carried out. It will be understood, however, that the specific details given in each example have been selected for the purpose of illustration and are not meant to be construed as a limitation on the present invention.

General Comments

Unless otherwise stated, all parts and percentages are by weight. Melting points (M.P.) were determined on an Electrothermal IA 9300 Digital Melting-point Apparatus. $^1$H and $^{13}$C NMR spectra were collected on a Bruker ACF 300 spectrometer with d-chloroform or $d_8$-THF as the solvent and tetramethylsilane as the internal standard. FT-IR spectra were recorded on a Bio-Rad FTS 165 spectrometer by dispersing the samples in KBr pellets. Mass spectra were measured on the V. G. Micromass VG7035, equipped with the MASPEC Data System. EI, ESI or FAB ion sources were used to obtain the mass fragments. UV-Visible and fluorescence spectra were obtained on a Shimadzu UV-NIR 3100 spectrophotometer and on a Shimadzu RF 5301PC luminescence spectrophotometer, respectively. Thermogravimetric analysis (TGA) was conducted on a TA Instruments TGA 2050 thermogravimetric analyser at a heating rate of 20° C./min and under an air flow rate of 75 mL/min. Differential scanning calorimetry (DSC) measurements were carried out on the Mettler Toledo DSC 822$^e$ system under $N_2$ and at a heating rate of 10° C./min. Elemental microanalyses were performed on a Perkin-Elmer 2400 elemental analyser (for C, H, N, and S). Rare earth contents were measured by titration with EDTA standard solution. Concentrated $HClO_4$ and $HNO_3$ were used to decompose the polymer samples before titration. ToF-SIMS analysis was carried out on an ION-TOF SIMS IV instrument (ION-TOF, GmbH, Germany). The polymer films were spin-cast from the THF solution onto ITO glass substrates. In the analysis, the primary ion beam (10 keV Ar$^+$) with a spot size of about 50 μm was rastered over an area of 500×500 μm$^2$ while keeping the total dose under $10^{13}$ ions/cm$^2$. The pressure in the analysis chamber was maintained at $1.0×10^{-9}$ Torr or lower during measurement. To reduce the charging effect, an electron flood gun was used for the charge neutralization. Gel permeation chromatography (GPC) analysis was conducted on a HP 1100 HPLC system equipped with the HP 1047A RI detector and the Agilent 79911GP-MXC columns, using standard polystyrene samples as the molecular weight references and THF as the eluent.

Example 1

Step 1

1,3-Bis(4-bromophenyl)propane-1,3-dione (DBDBM)

A mixture of ethyl-4-bromobenzoate and sodium methoxide in dry diethyl ether was stirred under an argon atmosphere. After 30 min, a solution of 4'-bromoacetophenone in dry diethyl ether was then added drop-wise under stirring. The reaction mixture was stirred for 48 h under argon at room temperature. The muddy mixture was acidified and filtered under reduced pressure. The filtrate was washed with water until pH reaches about 7. The crude product was decolourized with activated charcoal and further purified by recrystallization from ethyl acetate. The white needle crystals obtained was dried in a vacuum oven at 40° C. for 24 h. Yield: 5.40 g (28.3%). M.P.: 193.2-195.4° C. The structure was confirmed by EI-MS, $^1$H NMR, $^{13}$C NMR, FT-IR, UV-Vis spectroscopy, and elemental analysis.

Step 2

Eu(DBM)$_2$(DBDBM)phen

Dibenzoylmethane and 1,3-bis-(4-bromo-phenyl)-propane-1,3-dione were mixed in ethanol at 50-60° C. After addition of the aqueous sodium hydroxide, the mixture dissolved to a yellow-green, clear solution. The europium (III) chloride hexahydrate was dissolved in ethanol, and added drop-wise with stirring to the diketones solution at 65° C. Light-yellow solids formed after the addition of europium chloride solution. After stirring at the same temperature for another 20 min, a solution of anhydrous 1,10-phenanthroline in ethanol was added to the reaction mixture. After stirring for an additional ½ h, more light yellowish-green precipitates appeared. The mixture was allowed to stand overnight. The precipitates were filtered under reduced pressure and washed with ethanol for several times to remove the unchelated-ligands. The crude product was further purified by recrystallization from acetone/ethanol (1:1, volume ratio). The bright yellow crystal was dried at 50° C. in a vacuum oven for 24 h to afford 3.14 g (67.7%) of the monomer complex. M.P.: 150.2-152.6° C. The structure was confirmed by ESI-MS, FT-IR, UV-Vis spectroscopy, and elemental analysis.

Example 2

Rare Earth Compounds

Step 1

Anhydrous Europium Chloride (C1)

Under heating, 7.8 g (22 mmol) of europium oxide was reacted with hydrochloric acid (50 mL, 6.0 N) to form a yellow clear europium chloride solution. Ammonium chloride, 14.0 g (0.26 mol), was added to the above solution. The mixture was evaporated to give a white paste. It was then transferred to an evacuated reactor. Heated to about 180° C. under reduced pressure and maintained under the condition for about 2 h to drive off the water. The temperature was raised to about 400° C. over a period of 8 h to sublime all the ammonium chloride. After cooling down to room temperature, the reactor was filled with nitrogen. 10.6 g (yield: 93.7%) of white bulk solid were obtained. The product was carefully transferred to a dry bottle and sealed with wax.

Anhydrous Terbium Chloride (C2)

This compound was prepared from terbium oxide by following the procedure of Example 4, Step 1. Yield: 90.2%. The white bulk solid was carefully transferred to a dry bottle and sealed with wax.

Step 2

Europium Triisopropoxide (C3)

8.60 g (28.3 mmol) of europium chloride (anhydrous) were added to a dried 250 mL round bottom flask under a nitrogen atmosphere. After the addition of 40 mL of dried isopropanol, the mixture was stirred and heated to reflux temperature. The white powders dissolved to form a clear solution. In a separate dry flask, 1.95 g (84.8 mmol) of sodium pieces was reacted with 60 mL of dried isopropanol. At the end of the reaction, the formed sodium isopropoxide was diluted with 100 mL of dried benzene. The solution was added dropwise to the europium chloride solution. The reaction took place immediately after the addition of sodium isopropoxide, as characterized by the precipitation of white sodium chloride. After the addition, the reaction mixture was stirred for an additional 2 h at boiling temperature, and then cooled to the room temperature. The mixture was allowed to stand overnight to ensure the full separation of sodium chloride. The clear top-layer was europium isopropoxide in isopropanol/benzene. The concentration of $Eu(O^iPr)_3$ is 0.1337 M (yield: about 95.5%).

Terbium Triisopropoxide (C4)

This compound was prepared from terbium oxide by following the procedure of Example 4, Step 2. The concentration of $Tb(O^iPr)_3$ is 0.0891 M (yield: about 93.1%).

$Eu(DBM)_3mH_2O$ (C5)

β-Diketone ligand, dibenzoylmethane (6 mmol), was dissolved in 40 mL of ethanol in a flask at 50-60° C. The solution was neutralized with 1.0 N aqueous NaOH solution. After the pH value of the solution was about 6, the mixture was stirred at 70° C. for more than 2 h. A solution of $EuCl_3$ in ethanol (0.2 M, 10 mL) was added drop-wise with stirring to the mixture. After stirring at the same temperature for additional 2 h, the reaction mixture was allowed to cool down and stand overnight. The precipitates were filtered under reduced pressure and washed (i) with ethanol for several times to remove the unchelated-ligands, (ii) with Di water until $Cl^-$ could not be detected (monitored with $AgNO_3$ aqueous solution), (iii) with ethanol again. The crude product was further purified by recrystallization from acetone/ethanol (1:1, volume ratio). The bright yellow crystal was dried at 50° C. in a vacuum oven for 24 h to afford 3.41 g (69.1%) of the europium complex.

$Tb(acac)_3mH_2O$ (C6)

This complex was prepared by following the procedure for the preparation of C6 (Example 4, Step 2). It was a white powder. Yield: 2.33 g (57.4%).

Step 3

$Eu(TTA)_2(DBDBM)phen$

Thenoyltrifluoroacetone (TTA) was dissolved in dried THF. A solution of europium triisopropoxide was injected into the reaction flask. The reaction mixture was stirred for 1 h around 65° C. A solution of 1,3-bis-(4-bromophenyl)-propane -1,3-dione (DBDBM) in THF (5.0 mL) was then added drop-wise. After stirring at about 68° C. for 2 h, 1,10-phenanthroline anhydrous (phen) in THF was added. The resulting solution was concentrated and precipitated from n-hexane to afford a pale yellow solid. The product was dried in a vacuum oven for 24 h. Yield: 0.542 g (70.1%). M.P.: 184.1-186.3° C. The structure was confirmed by ESI-MS, FT-IR, UV-Vis spectroscopy, and elemental analysis.

Example 3

Step 1

2,7-Dibromo-9,9-di-n-hexylfluorene

1-Bromohexane was added dropwise to a mixture, consisting of 2,7-dibromofluorene and a catalytic amount of triethylbenzylammonium chloride in DMSO and aqueous NaOH. The resulting mixture was stirred for 5 h at room temperature. Excess amount of acetyl acetate was then added to the reaction mixture. The NaOH precipitate was filtered off. The organic layer was concentrated, and then washed with 0.5 N HCl and distilled water. After dried over anhydrous $MgSO_4$ overnight, the solvent was removed by rotary evaporation. The yellow crude product was purified by flash column chromatography using n-hexane as the eluent, followed by recrystallization from methanol. 14.3 g (yield: 95.9%) of 2,7-dibromo-9,9-di-n-hexylfluorene was collected as white crystal. M.P.: 67.6-68.1° C. The structure was confirmed by EI-MS, $^1H$ NMR, $^{13}C$ NMR, FT-IR, UV-Vis spectroscopy, and elemental analysis.

Step 2

9,9-Di-n-hexylfluorene-2,7-diboronic acid

The solution of 2,7-dibromo-9,9-di-n-hexylfluorene in THF (50 mL) was added to a dry flask charged with magnesium turnings under an argon atmosphere. A few pieces of iodine were added to initiate the reaction. The formed Grignard reagent was added slowly to a solution of trimethyl borate in THF at −78° C. After the addition, the reaction mixture was allowed to warm up slowly and stirred continuously at room temperature for 72 h. The resulting mixture was poured into crushed ice containing 5% (w/w) sulphuric acid under stirring. The mixture was extracted with diethyl ether, washed with water and dried over $MgSO_4$ overnight. The crude diboronic acid was purified by recrystallization from the mixture of hexane and acetone to afford 10.90 g of 9,9-di-n-hexylfluorene-2,7-diboronic acid as white crystalline powders (yield: 62.9%). M.P.: to 300° C. The structure was confirmed by FAB-MS, $^1H$ NMR, $^{13}C$ NMR, FT-IR, UV-Vis spectroscopy, and elemental analysis.

Step 3

9,9-di-n-hexylfluorene-2,7-bis(trimethylene boronate)

9,9-di-n-hexylfluorene-2,7-diboronic acid was refluxed with 1,3-propandiol in toluene for 6 h. After the removal of solvent, the residue was dissolved in chloroform, washed with water and dried over anhydrous magnesium sulphate. After the chloroform was removed under reduced pressure, the crude product was recrystallized from n-hexane to afford 9,9-di-n-hexylfluorene-2,7-bis(trimethylene boronate) as white square-shaped crystals (yield: 4.42 g, 88.0%). M.P.: 123.2-124.5° C. The structure was confirmed by EI-MS, $^1$H NMR, $^{13}$C NMR, FT-IR, UV-Vis spectroscopy, and elemental analysis.

Step 4

Copolymer Complex 1 [Equation 3]

Under a nitrogen atmosphere, the europium-containing monomer complex $Eu(TTA)_2$(DBDBM)phen was dissolved in degassed boiling toluene in a small flask wrapped with aluminium foil. After the yellow clear solution was cooled to about 70° C., a mixture of 9,9-di-n-hexyl-9H-fluorene-2,7-bis(trimethylene boronate), 2,7-dibromo-9,9-dihexylfluorene and the catalyst $Pd(PPh_3)_4$ was then added. A degassed aqueous solution of potassium carbonate was finally added to the reactor. The mixture was stirred vigorously at 80-90° C. for 72 h under a nitrogen atmosphere. The resulting solution was filtered to exclude the insoluble species and added dropwise into stirring methanol to precipitate the polymer. The material was washed continuously with acetone for 2 days in a Soxhlet extractor to remove the complex residues. The product was dried under reduced pressure overnight. Yield: 73 mg (12.2 %). The number-average molecular weight ($M_n$) is about $3.00 \times 10^3$. The copolymer complex was characterized by GPC, FT-IR, UV-Vis, ToF-SIMS, DSC and TGA.

Example 4

Copolymer Complex 2 [Equation 3]

The procedure is similar to that described in Example 3, except $Eu(DBM)_2$(DBDBM)phen was used instead, the concentration of $K_2CO_3$ was reduced, and a phase-transfer catalyst (PTC), benzyltriethylammonium chloride, was used in the coupling copolymerization. Different from that of copolymer complex 1, decomposition of the europium complex did not occur during copolymerization, as indicated by the clear solution mixture obtained. Yield: 0.13 g (21.8 %). $M_n=1.43 \times 10^4$, $M_w$(weight-average molecular weight)$=2.18 \times 10^4$, PDI (polydispersity index)=1.53. The copolymer complex was characterized by GPC, $^1$H NMR, $^{13}$C NMR, FT-IR, UV-Vis, ToF-SIMS, DSC and TGA.

Example 5

Step 1

Anhydrous Terbium Chloride

This compound was prepared from terbium oxide by following the procedure of Example 2, Step 1. Yield: 90.2%. The white bulk solid was carefully transferred to a dry bottle and sealed with wax.

Step 2

Terbium Triisopropoxide

This compound was prepared from terbium oxide by following the procedure of Example 2, Step 2. The concentration of $Tb(O^iPr)_3$ is 0.0891 M (yield: about 93.1%).

Example 6

Step 1

Methyl 3,5-dibromobenzoate

DMSO was bubbled with argon, and then added to a nitrogen-purged flask. After the potassium hydroxide powder was added to the flask, the mixture was vigorously stirred under the argon atmosphere for one hour. 3,5-dibromobenzoic acid was added to the mixture. The reaction mixture was kept under stirring at room temperature for 30 min. Excess amount of iodomethane was poured into the above mixture. The mixture was stirred at room temperature for 12 h. The resulting mixture was added to ice water with vigorous stirring. The precipitates were obtained by filtration. The crude product was recrystallized from ethyl acetate to afford methyl 3,5-dibromobenzoate as light brown needle crystals. Yield: 0.78 g (88.7%). M.P.: 63.8-64.2° C. The structure was confirmed by EI-MS, $^1$H NMR, $^{13}$C NMR, FT-IR, UV-Vis spectroscopy, and elemental analysis.

Step 2

Poly[2,7-(9,9-dihexylfluorene)-co-5-(methoxycarbonyl)-phenylene-1,3-diyl] (2:1)

Under an argon atmosphere, 9,9-di-n-hexylfluorene-2,7-bis(trimethylene boronate), methyl 3,5-dibromobenzoate and 2,7-di bromo-9,9-di-n-hexylfluorene were mixed together with $Pd(PPh_3)_4$ in a small flask. Degassed aqueous solution of potassium carbonate and toluene (3:5, volume ratio) were added to the reactor. The mixture was stirred vigorously at 80-90° C. for 72 h under an argon atmosphere. The resulting solution was added dropwise into stirring methanol to precipitate the polymer. The fibrous solid was collected by filtration, washed with methanol and water. The material was washed continuously with acetone for 2 days in a Soxhlet extractor to remove the oligomers and catalyst residues. The product was dried under reduced pressure overnight. It was a grey flocculent solid (yield: 88.1%). $M_n=1.37 \times 10^4$, $M_w=3.02 \times 10^4$, PDI=2.20. The copolymer was characterized by GPC, $^1$H NMR, $^{13}$C NMR, FT-IR, UV-Vis, DSC and TGA.

Step 3

Poly[2,7-(9,9-di hexylfluorene)-co-5-carboxy-phenylene-1,3-diyl] (2:1)

Under the protection of argon, poly[2,7-(9,9-dihexylfluorene)-co-5-(methoxycarbonyl)-phenylene-1,3-diyl] (2:1) was dissolved in THF and refluxed with a solution of sodium hydroxide in methanol. With the hydrolysis in progress, the solution became opaque, and a substantial amount of insoluble solid appeared after 24 h. The reaction was allowed to proceed for another 24 h. The reaction mixture was poured into 100 mL of distilled water with vigorous stirring to form a milky solution. After acidified with diluted hydrochloric acid, the resulting white material was isolated by filtration and washed thoroughly with distilled water. The polymer was dried in a vacuum oven at 50° C. for 24 h. It was a light yellow flocculent solid (yield: 90.6%). $M_n32$ $1.65\times10^4$, $M_w=3.34\times10^4$, PDI=2.03. The copolymer was characterized by GPC, $^1$H NMR, $^{13}$C NMR, FT-IR, UV-Vis, DSC and TGA.

Step 4

Copolymer Complex 3 [Equation 6]

All the glassware was pre-baked at 110° C., cooled under vacuum, and purged with nitrogen. A solution of terbium triisopropoxide was injected into a flask and then diluted with dried THF. The solution was warmed to 60° C. in an oil bath. A solution of poly[2,7-(9,9-dihexylfluorene)-co-5-carboxyphenylene-1,3-diyl] (2:1) in dried THF was added dropwise into the flask by means of a syringe. The reaction mixture was refluxing for half. Two equivalents of acetyl acetone (acac) was dissolved in THF and added dropwise into the reaction mixture. After 5 h, the last ligand, 1,10-phenanthroline (anhydrous) in THF was added. The resulting solution was concentrated and dropped into water to precipitate the polymer. The crude product was washed thoroughly with hot ethanol to remove the residue ligands and small molecular complexes. The polymer was dried in a vacuum oven at 50° C. for 24 h. Yield: 53%. $M_n=1.87\times10^4$, $M_w=5.11\times10^4$, PDI=2.73. The copolymer complex was characterized by GPC, FT-IR, UV-Vis, ToF-SIMS, DSC and TGA.

Example 7

Step 1

9,9-Diethylhexylfluorene

The fluorene powder was dissolved in 120 mL of dried THF and then purged with argon for half an hour. A solution of n-butyl lithium in hexane (1.60M) was added dropwise into the reactor. The resulting solution was stirred at −78° C. for about one hour under argon atmosphere. A solution of 1-ethylhexyl bromide in THF was added dropwise and stirring continued at −78° C. for about two hours. Ammonium chloride was added to the reaction mixture. The mixture was extracted with diethyl ether and dried over anhydrous magnesium sulfate. After the removal of the residue solvents and the excess 1-ethylhexyl bromide under vacuum, an oily product was afforded. Yield: 17.26 g (82.90%). The structure was confirmed by EI-MS, $^1$H NMR, $^{13}$C NMR, FT-IR, and UV-Vis spectroscopy.

Step 2

2,7-Dibromo-9,9-diethylhexylfluorene 9,9-Diethylhexylfluorene was added to a flask wrapped with aluminum foil and diluted with dichloromethane. A catalytic amount of 12 was added into the flask. The solution was cooled with ice bath and bromine in dichloromethane was added. The solution was stirred at room temperature for 20 h in the dark. An aqueous solution of potassium hydroxide was added. It was stirred vigorously until the red colour of the mixture disappeared. After removal of the solvent, 23.38 g (80%) of orange oily product was obtained. The structure was confirmed by EI-MS, $^1$H NMR, $^{13}$C NMR, FT-IR, and UV-Vis spectroscopy.

Step 3

9,9-Diethylhexylfluorene-2,7-dibronic acid

This compound was prepared from 2,7-dibromo-9,9-diethylhexylfluorene by following the procedure of Example 3, Step 2, to obtain a light brown solid. Yield: 7.41g (77.4%). M.P.: 220.5-222.7° C. The structure was confirmed by FAB-MS, $^1$H NMR, $^{13}$C NMR, FT-IR, UV-Vis spectroscopy, and elemental analysis.

Step 4

9,9-Di-ethylhexyl-9H-fluorene-2,7-bis(trimethylene boronate)

This compound was prepared from 9,9-diethylhexylfluorene-2,7-dibronic acid by following the procedure of Example 3, Step 3. Removal of solvent afforded about 2.25 g (96.4%) of yellow oil. The structure was confirmed by EI-MS, $^1$H NMR, $^{13}$C NMR, FT-IR, UV-Vis spectroscopy, and elemental analysis.

Step 5

Poly[2,7-(9,9-diethylhexyl-9H-fluorene)-co-5-(methoxycarbonyl)-phenylene-1,3-diyl]

2,7-Bis(trimethylene boronate)-9,9-diethylhexylfluorene, 2,7-dibromo-9,9-diethylhexylfluorene, methyl 3,5-dibromobenzoate and Pd(PPh$_3$)$_4$ were mixed together in a small flask. An aqueous solution of potassium carbonate and toluene were added to the reactor. The reaction mixture was stirred at 85-90° C. for 72 h. The polymer was collected as grey flocculent solid, after precipitation from methanol and washed with acetone in a Soxhlet extractor (yield: 82.8%). $M_n=1.21\times10^4$, $M_w=3.09\times10^4$, PDI=2.54. The copolymer was characterized by GPC, $^1$H NMR, $^{13}$C NMR, FT-IR, UV-Vis spectroscopy, DSC and TGA.

Example 8

Poly[2,7-(9,9-diethylhexyl-9H-fluorene)-co-5-carboxy-phenylene-1,3-diyl]

Under the protection of argon, poly[2,7-(9,9-diethylhexyl-9H-fluorene)-co-5-(methoxycarbonyl)-phenylene-1,3-diyl] was dissolved in THF and refluxed with a 5-10 wt % methanol solution of sodium hydroxide for 72 h. After acidified with diluted hydrochloric acid, the resulting white material was isolated and washed with water. It was collected as an off-white solid (yield: 91.0%). $M_n=1.76\times10^4$, $M_w=3.83\times10^4$, PDI=2.18. The copolymer was characterized by GPC, $^1$H NMR, $^{13}$C NMR, FT-IR, UV-Vis spectroscopy, DSC and TGA.

Example 9

Copolymer Complex 4 [Equation 6]

A solution of europium triisopropoxide was introduced into a dry flask. After the solution was warmed up to 60° C., a dry THF solution of poly[2,7-(9,9-diethylhexyl-9H-fluorene)-co-5-carboxy-phenylene-1,3-diyl] was added by means of a syringe. A calculated amount of dibenzoylmethane (DBM) was dissolved in THF and added dropwise into the reaction mixture. The last ligand, 1,10-phenanthroline (anhydrous), THF was added. The resulting solution was concentrated and poured into water to precipitate the polymer. The light yellow solid was washed thoroughly with hot ethanol and dried under reduced pressure (yield: 72%). $M_n=1.99\times10^4$, $M_w=4.14\times10^4$, PDI=2.08. The copolymer complex was characterized by GPC, $^1$H NMR, $^{13}$C NMR, FT-IR, UV-Vis spectroscopy, ToF-SIMS, DSC, TGA and elemental analysis.

Example 10

Fabrication of Polymer Light-emitting Diodes (PLEDs)

A substrate (patterned with indium-tin oxide (ITO) on glass) was cleaned by ultrasonication in acetone, isopropanel, methanol, and deionized water, in that order. It was then etched by a 100 W oxygen plasma. A film was deposited immediately on the cleaned ITO substrate by spin-coating from a solution containing the copolymer complex of this invention. The solvent was removed completely under vacuum. Lithium fluoride (LiF) was deposited as a cathode buffer layer, followed by the thermal deposition of cathode. Then the device was capsulated with a glass plate and sealed with epoxy glue under a nitrogen atmosphere. By applying voltage on the resulted device, EL light emission from the copolymer complex was obtained. The performance of the devices were characterized by current-voltage relationship, luminance-voltage relationship, turn-on voltage, maximum brightness, EL spectrum, luminance efficiency, durability (lifetime) and other parameters.

Example 11

Step 1

5,5'-Dicarboxy-2,2'-bipyridine (M1)

To a stirred solution of sulfuric acid (97%, 125 mL), 5.0g (27.1 mmol) of 5,5'-dimethyl-2,2'-bipyridine was added. 24 g (81.5 mmol) of potassium dichromate was then added in small portions, such that the temperature remained between 70 to 80° C. After all the dichromate was added, the reaction was stirred until the temperature fell below 40° C. The reaction mixture was poured into 800 mL of ice water and filtered. The solid was washed with water until the green colour of the filtrate disappeared and allowed to dry. The resulting light yellow solid was then further purified by refluxing it in 170 mL of 50% nitric acid for 4 h. This solution was poured over ice, diluted with 1 L of water and cooled to 5° C. The precipitate was filtered, washed with water, then acetone and allowed to dry at 100° C. under vacuum giving 6.03 g (91.0%) of product as a fine white solid. M. P.>400° C.

4,4'-Dicarboxy-2,2'-bipyridine (M2)

Following the procedure of Example 1 Step 1, 4,4'-dicarboxy-2,2'-bipyridine was prepared from 5,5'-dimethyl-2,2'-bipyridine as white powder. Yield: 6.09 g (91.8%). M. P.>325° C.

Step 2

2,2'-Bipyridine-5,5'-dicarbonyl dichloride (M3)

1.0 g (4.1 mmol) of 5,5'-dicarboxy-2,2'-bipyridine (white powder) was added to a dried flask under the argon atmosphere. 20 mL of thionyl chloride and 0.1 mL of dried pyridine were added into the flask. The mixture was refluxed under argon atmosphere for 48 h. The excess thionyl chloride was distilled off. The crude product was recrystallized from 100 mL of n-heptane to afford 0.83 g (72.4%) of white needle crystal.

2,2'-Bipyridine-4,4'-dicarbonyl dichloride (M4)

Following the procedure of Example 1 Step 2, 2,2'-bipyridine-4,4'-dicarbonyl dichloride was prepared from 4,4'-dicarboxy-2,2'-bipyridine as white crystal. Yield: 5.87 g (84.8%).

Step 3 p-Bromobenzoic hydrazide (M5)

9.16 g (40 mmol) of ethyl 4-bromobenzonate and 40 mL of methanol was added to a dried flask. The solution was stirred and bubbled with argon for half an hour. 5.82 mL (120 mmol) of hydrazine monohydrate was injected into the solution. The solution was refluxed under the argon atmosphere for 18 h. White needle crystal appeared, after the reaction mixture was cooled to room temperature. It was filtered under vacuum, washed with methanol and dried in vacuum oven at 40° C. for 24 h. Yield: 8.26 (96.0%). M.P.: 159.6-161.3° C.

Step 4

5,5'-Bis(4-bromophenyl hydrazine)-2,2'-bipyridine (M6)

2.96 g (10.5 mmol) of 2,2'-bipyridine-5,5'-dicarbonyl dichloride was dissolved with 70 mL of dry pyridine under the atmosphere of argon in a dried reactor. 4.53 g of 4-bromobenzoic hydrazide was dissolved with about 40 mL of dry pyridine and then added dropwise to the reactor. The colour of mixture turned to light brown, and much powder appeared. It was refluxed for about 24 h. The mixture was poured into 300 mL of distilled water, filtered under reduced pressure and washed repeatedly with water. The light yellow powder was dried in vacuum oven at 70° C. for 48 h. Yield: 5.54 g (82.4%).

4,4'-Bis(4-bromophenyl hydrazine)-2,2'-bipyridine (M7)

Following the procedure of Example 1 Step 4, 4,4'-bis(4-bromophenyl hydrazine)-2,2'-bipyridine was prepared from 2,2'-bipyridine-5,5'-dicarbonyl dichloride and p-bromobenzoic hydrazide as white powder. Yield: 1.68 g (52.7%). M.P.: 368.2-370.2° C.

Step 5

5,5'-Bis[2-(4-bromophenyl)-1,3,4-oxadiazoyl]-2,2'-bipyridine (M8)

1.68 g (2.6 mmol) of 5,5'-bis(4-bromophenyl hydrazine)-2,2'-bipyridine was added to a dried flask under argon atmosphere. After the addition of 20 mL of thionyl chloride, the mixture was refluxed under argon atmosphere for about 8 h. The excess thionyl chloride was rotary evaporated and the residue was washed with water repeatedly. The light yellow powder was collected and dried in vacuum heating oven at 40° C. for about 48 h. Yield: 1.34 g (84.8%). M. P.>300° C.

4,4'-Bis[2-(4-bromophenyl)-1,3,4-oxadiazoyl]-2,2'-bipyridine (M9)

Following the procedure of Example 1 Step 5, 4,4'-bis[2-(4-bromophenyl)-1,3,4-oxadiazoyl]-2,2'-bipyridine was prepared from 4,4'-bis(4-bromophenyl hydrazine)-2,2'-bipyridine as white powder. Yield: 1.56 g (98.5%). M.P.: 357.1-358.6° C.

Example 12

Synthesis of the Monomers of Carbazole Derivative

Step 1

3,6-dibromo-9-(2-ethylhexyl)-carbazole (M10)

To a solution of 3,6-dibromocarbazole (3.0 g, 8.95 mmol) in 25 mL of dried DMF was added potassium carbonate (2.47 g, 17.9 mmol). The mixture was stirred and degassed for 1 h, after which 1-bromo-2-ethylhexane (2.70 g, 13.4 mmol) was added dropwise, followed by refluxing for 2 days. The reaction mixture was poured into 100 mL of distilled water and extracted with chloroform. The combined organic layer was dried with anhydrous magnesium sulfate. After removal of the solvent and unreacted 2-ethylhexyl bromide under reduced pressure, the residue was purified by column chromatography on silica gel using hexane and ethyl acetate as the eluent to afford 3,6-dibromo-9-(2-ethylhexyl)-carbazole as a waxy solid. Yield: 3.02 g (77.2%), M.P.: 62.4-63.6° C.

2,7-Dibromo-9-(2-ethyl hexyl)-carbazole (M11)

A mixture of 2,7-dibromocarbazole (3.0 g, 8.95 mmol), 1-bromo-2-ethylhexane (2.70 g, 13.4 mmol), tetra-n-butylammonium hydrogen sulfide (0.1 g), and NaOH (0.54 g, 13.5 mmol) in acetone (30 mL) was refluxed for 9 h. After the reaction, the acetone was removed under vacuum and the residue was extracted with toluene. The combined organic layer was washed with a saturated NaCl aqueous solution, and dried over $MgSO_4$. After removal of the solvent, the residue was purified by column chromatography on silica gel using hexane as the eluent to afford 2,7-dibromo-9-(2-ethylhexyl)-carbazole as a white powder. Yield: 2.46 g (62.9%). M.P.: 95-97° C.

Step 2

3,6-Bis(4,4,5,5-tetramethyl-1,3,2-dioxaborolan-2-yl)-9-ethylhexylcarbazole (M12)

To a solution of 3,6-dibromo-9-ethylhexyl-carbazole (4.37 g, 10.0 mmol) in THF (50 ml) at −78, 20 ml of n-butyllithium (1.6 M in hexane) was added by means of a syringe. The mixture was stirred at −78 for 2 h. 2-isopropoxy-4,4,5,5-tetramethyl-1,3,2-dioxaborolane (25 ml) was added rapidly to the solution, and the mixture was stirred at −78 for another 2 h. The resulting mixture was warmed to room temperature and further stirred for 24 h. The mixture was poured into water and extracted with diethyl ether. The combined organic layer was washed with water, a saturated NaCl aqueous solution and dried over $MgSO_4$. After removal of the solvent by distillation, the residue was purified by column chromatography on silica gel with ethyl acetate and hexane (7:100) as the eluent to afford the title product as a pale-white solid. Yield: 2.63 g (48.9%).

Example 13

Synthesis of a Conjugated Copolymer by Suzuki Reaction Method (P1)

Under an argon atmosphere, 2,7-bis(trimethylene boronate)-9,9-diethylhexylfluorene (1.0 mmol), 5,5'-bis[2-(4-bromophenyl)-1,3,4-oxadiazoyl]-2,2'-bipyridine (1.0 mmol) and $Pd(PPh_3)_4$ (12 mg) were mixed together in a small flask. 3 mL of degassed aqueous solution of potassium carbonate (2.0 M) and 5 mL of DMF were added to the reactor. The reaction mixture was stirred at 85-90° C. for 72 h. The polymer was collected as light yellow solid, after precipitation from methanol and washed with acetone in a Soxhlet extractor. Yield: 0.51 g (65.9%).

Example 14

Synthesis of the Copolymer Complex in Non-Aqueous Phase (P2)

All the glassware was pre-baked at 110° C., cooled under vacuum, and purged with nitrogen. 0.3 mmol of europium triisopropoxide in the mixed solvent of benzene and isopropanol (1:1, volume ratio) was injected into a flask and then diluted with dried THF (3 mL). The solution was warmed to 60° C. in an oil bath. A solution of the functional monomer (P1: 0.23 g, 0.3 mmol) in dried THF was added drop-wise into the flask by means of a syringe. The reaction mixture was kept under stirring and refluxing for half an hour under an argon atmosphere. Two equivalents of thenoyltrifluoroacetone (TTA)] was dissolved in 5 mL of THF and added drop-wise into the reaction mixture over a period of 15 min. The resulting solution was concentrated and dropped into water to precipitate the polymer. The crude product was washed thoroughly with hot ethanol to remove the residual ligands and small molecular complexes. The polymer was dried in a vacuum oven at 50° C. for 24 h. Yield: 0.27 g (56.5%).

Example 15

Copolymer Complex in Aqueous Phase-I (P3)

The functional copolymer (P1: 0.3 mmol) and β-diketone ligand, dibenzoylmethane (DBM, 0.9 mmol), were dissolved in a mixture of 10 mL of THF and 2 mL of ethanol in a flask at 50-60° C. The solution was netralized with aqueous NaOH solution. After the pH value of the solution was about 6, the mixture was stirred at 70° C. for more than 2 h. A solution of $EuCl_3$ in ethanol (0.2 M, 1.5 mL) was added drop-wise with stirring to the mixture. After stirring at the same temperature for additional 2 h, the reaction mixture was poured into 80 mL of methanol. The precipitates were collected by filtration and washed with ethanol for several times to remove the unchelated-ligands, then with DI water (20 mL×5) until $Cl^-$ could not be detected (monitored with $AgNO_3$ aqueous solution. The crude product was further washed continuously with acetone for 2 days in a Soxhlet extractor to remove the residue ligands, and the europium complexes (small molecular weight). Yield: 0.21 g (43.9%).

Example 16

Copolymer Complex in Aqueous Phase-II (P4)

0.1 mmol of the functional copolymer (P1) and an excess amount of the tri(β-diketonato) europium (C5) were dissolved in a mix-solvents of 8 mL of THF and 2 mL of ethanol in a flask. The solution was refluxed for 2 d. The resulting solution was added drop-wise into stirring methanol (80 mL) to precipitate the copolymer complex. The crude product was dissolved in THF and then reprecipitated in an excess volume of methanol under vigorous stirring. This procedure was repeated 2-3 times. The product was dried under reduced pressure overnight. It was a pale yellow solid (Yield: 73 mg, 45.8%).

Example 17

Ditetrazole Monomer

Step 1

Synthesis of 2,7-dicyano-9,9-dihexylfluorene (M13)

A mixture of 2,7-dibromo-9,9-dihexylfluorene (10 mmol) and CuCN (35 mmol) in NMP (30 mL) was purged with argon and refluxed for 4 h. The hot reaction mixture (~120° C.) was then slowly poured into a stirred acidified aqueous $FeCl_3$ solution. The mixture was stirred for additional 20 min at 90° C. and then extracted with toluene. The combined organic layer was washed with HCl until the dark heavy organic layer disappeared, and then with water, 10% NaOH solution, and water again until pH reaches about 7. It was dried over anhydrous $MgSO_4$. After removal of the solvent, the residue was purified by column chromatography on silica gel using AcOEt and hexane (20/80) as the eluent, followed by recrystallization from hexane to afford colourless crystals in yield of 3.21 g (83.35%). M.P.=116-118° C.

3,6-Dicyano-9-(2-ethylhexyl)-carbazole (M14)

A mixture of 3,6-dibromo-9-(2-ethylhexyl)-carbazole (M17: 4.37 g, 10 mmol) and dried copper (I) cyanide (35 mmol) in dry DMF (50 mL) was heated at reflux temperature under argon atmosphere for 70 h. The reaction mixture was poured into ice-water. The precipitate was filtered off and washed with water. The collected solid was further stirred in water containing ethylene-diamine (5 mL) for 1 h, then filtered off and washed with water again. The solid was stirred in the presence of sodium cyanide (4.0 g) in water (70 mL) for 1.5 h. The dinitrile was filtered off, washed with water, and dried to give a tan powder. Yield: 3.04 g (92.4%).

Step 2

9,9-Dihexylfluorene-2,7-ditetrazole (M15)

A mixture of 2,7-dicyano-9,9-dihexylfluorene (5.77 g, 15 mmol) and $NaN_3$ (2.34 g, 36 mmol) in anhydrous toluene (40 mL) was purged with argon. 10 mL of $(n-Bu)_3SnCl$ was added to the mixture by means of a syringe. The mixture was refluxed for 72 h. The solution was then acidified with concentrated HCl and further stirred at room temperature for 24 h. After removal of the solvents, the residue was dissolved with ethyl acetate and washed with water. The organic layer was dried over $MgSO_4$. The crude product was purified by column chromatography using AcOEt/hexane (33/67, v/v) followed by acetone as the eluent, and recrystallization from acetyl acetate. 4.85 g (68.8%) of 9,9-dihexylfluorene-2,7-ditetrazole was collected as white crystal. M.P.=237-240° C.

Example 18

Tetrazole Route to Alternating Copolymer of Fluorene, Oxadiazole and Bipyridine (P5)

2.5 mmol of 2,2'-bipyridine-5,5'-dicarbonyl dichloride (white crystal) was dissolved in 20 mL of anhydrous. A solution of 9,9-dihexylfluorene-2,7-ditetrazole in 20 mL of anhydrous pyridine was added to the above solution. The resulting mixture was refluxed for 4 h under argon. The resulting solution was concentrated to about 10 mL, and then precipitated from 500 mL of ice water. The precipitate was filtered off and washed water. It was further purified by reprecipitation from DMF solution to water and then dried at 50° C. under vacuum for 24 h. Yield: 1.17 g (93%).

Example 19

Post-chelation of P5 to $Tb^{3+}$ in Non-aqueous Phase (P6)

This copolymer complex was synthesized by the coordination of the copolymer ligand (P5) with a highly reactive terbium salt, terbium triisopropoxide (C4), by following the procedure similar to that of Example 6, except the solvent was changed from THF to DMF.

Example 20

Post-chelation of P5 to $Tb^{3+}$ in Aqueous Phase-I (P7)

This copolymer complex was synthesized by the coordination of the copolymer ligand (P5), together with acetyl acetone (acac), to the terbium ion by following the procedure similar to that of Example 7, except the solvent was changed from THF to DMF.

Example 21

Post-chelation of P5 to $Tb^{3+}$ in Aqueous Phase-II (P8)

This copolymer complex was synthesized by coordination of the copolymer ligand (P5) with an excess amount of the tri(acetyl acetonato) terbium (C6), by following the procedure similar to that of Example 8, except the solvent was changed from THF to DMF.

The invention claimed is:

1. A copolymer complex of the formula:

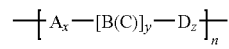

wherein $[A_x\text{-}[B(C)]_y\text{-}D_z]$ a single unit of the copolymer complex that is repeated n times, wherein n is an integer greater than one, and wherein the single unit comprises a conjugated backbone coordinated to a complex (C) comprising rare earth metal(s); x, y and z are numbers greater than zero such that x=y+z; A is independently selected from a group consisting of: fluorene, carbazole, oxadiazole, triphenylamine, and derivatives thereof; B is a functional ligand selected from the group consisting of: benzoic acid, 1,3-diphenylpropane-1,3-dione, 1,10-phenanthrolne, 2,2-bipyridine, and derivatives thereof; and D is independently selected from the group consisting of: fluorene, carbazole, oxadiazole, triphenylamine, and derivatives thereof.

2. The copolymer complex according to claim 1, which is a random or block copolymer complex.

3. The copolymer complex according to claim 1, wherein D is different from A.

4. The copolymer complex according to claim 1, wherein A is represented by the formula:

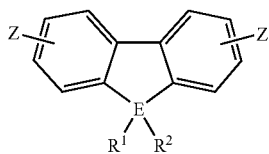

wherein $R^1$ and $R^2$ are the same or different and are linear or branched $C_{1-20}$ alkyl or alkoxy groups or at least one of $R^1$ and $R^2$ is absent, Z is a point of connection to a further block of the copolymer, E is a carbon atom (C) or a nitrogen atom (N), and when E is a nitrogen atom Z is at positions 3 and 6, and when E is a carbon atom Z is at positions 2 and 7.

5. The copolymer complex according to claim 4, wherein A is a fluorene group, E is a carbon atom and $R^1$ is the same as $R^2$.

6. The copolymer complex according to claim 4, wherein A is a carbazole group, E is a nitrogen atom and $R^2$ is absent.

7. The copolymer complex according to claim 4, wherein $R^1$ and $R^2$, independently, are selected from the group consisting of: n-hexyl group, 2-ethylhexyl group, n-octyl group, n-decyl group, n-dodecyl group, 2-hexyldecyl group, n-octadecyl and corresponding alkoxyl groups.

8. The copolymer complex according to claim 1, wherein [B(C)] is an organic complex, and C is represented by the formula:

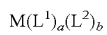

wherein M is a rare earth metal ion; $L^1$ is selected from the group consisting of an enolate, carboxylate, sulfonate, alkoxide, amide and derivatives thereof; $L^2$ is a neutral ligand selected from the group consisting of: 1,10- phenanthroline (phen), 2,2-bipyridine group (bpy), 2,6-di(pyridine-3-yl)pyridine (tpy), phosphine oxide and derivatives thereof; a is an integer in the range of 2-4; and b is 0 or 2.

9. The copolymer complex according to claim 1, wherein [B(C)] is of the formula:

wherein M is an independent rare earth metal ion, $L^1$ is selected from the group consisting of:
enolate, carboxylate, sulfonate, alkoxide, amide and derivatives thereof; a is an integer in the range of 2-4.

10. The copolymer complex according to claim 8, wherein B is a derivative of the 1,10-phenanthroline or 2,2-bipyridine group of the formulae:

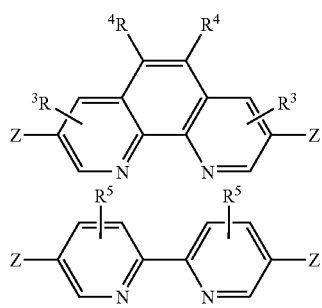

wherein $R^3$, $R^4$, and $R^5$ are independent groups selected from the group consisting of:
hydrogen, alkyl, perfluoroalkyl, alkoxy, aryl and aryloxy groups; and Z is a point of connection to a further block of the copolymer.

11. The copolymer complex according to claim 10, wherein the alkyl or alkoxy group is linear, branching or cyclic, with carbon atoms in the range of $C_{1-20}$.

12. The copolymer complex according to claim 10, wherein $R^3$, $R^4$, and $R^5$ are selected from the group consisting of: methyl, ethyl, butyl, hexyl, octyl and their corresponding perfluoroalkyl or alkoxyl groups.

13. The copolymer complex according to claim 10, wherein the aryl or aryloxy group is selected from the group consisting of: phenyl, alkylphenyl, naphthyl, fluorenyl and corresponding aryloxy groups.

14. The copolymer complex according to claim 1, wherein the organic complex [B(C)] is selected from the group consisting of:

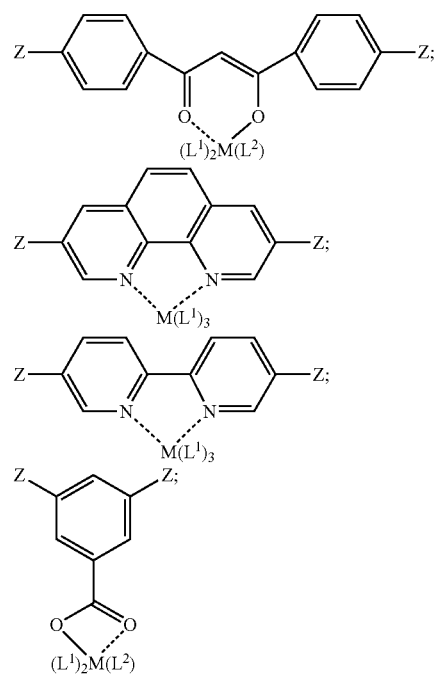

and wherein Z is a point of connection to a further block of the copolymer; M is a rare earth metal ion; $L^1$ is an enolate, carboxylate, sulfonate, alkoxide, or amide ligand; $L^2$ is an independent neutral ligand selected from the group comprising 1,10-phenanthroline (phen), 2,2-bipyridine group (bpy), 2,6-di(pyridine-3-yl)pyridine (tpy), phosphine oxide and derivatives thereof.

15. The copolymer complex according to claim 1, wherein D is selected from the group consisting of a derivative of oxadiazole and a derivative of triphenylamine of the following formulae:

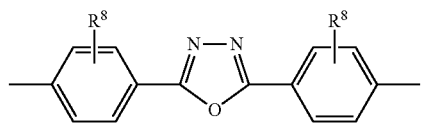

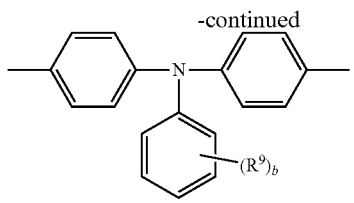

wherein $R^8$ is independently selected from the group consisting of: hydrogen, alkyl, perfluoroalkyl, alkoxy, aryl and aryloxy groups; $R^9$ is independently selected from hydrogen, alkyl, alkoxy, carboxyalkyl or carboxyaryl, wherein said alkyl, perfluoroalkyl, alkoxy, aryl, aryloxy, carboxyalkyl, and carboxyaryl groups contain 1 to 20 carbon atoms and b is an integer in the range of 0 to 3.

16. The copolymer complex according to claim 15, wherein the alkyl or alkoxy group is linear, branching or cyclic, with carbon atoms in the range $C_{1-20}$.

17. An organic complex, wherein the organic complex is selected from the group consisting of:

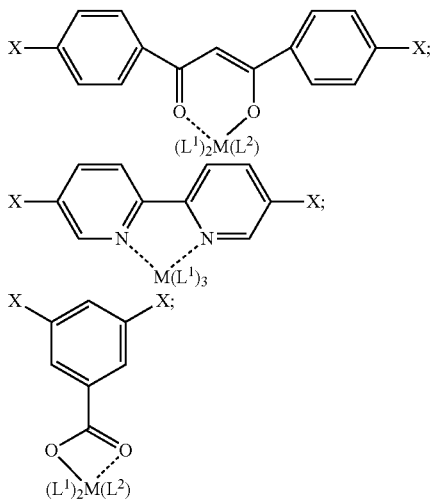

and wherein X is independently in each occurrence a halide; M is a rare earth metal;

$L^1$ is an enolate, carboxylate, sulfonate, alkoxide, or amide ligand or corresponding anions; $L^2$ is an independent neutral ligand selected from the group comprising 1,10-phenanthroline (phen), 2,2-bipyridine group (bpy), 2,6-di(pyridine-3-yl)pyridine (tpy), phosphine oxide and derivatives thereof.

18. A method of producing a copolymer complex according to claim 1, comprising synthesizing a conjugated backbone $[A_x-B_y-D_z]$, and performing a post-chelation of the backbone to a complex C comprising a rare earth metal ion and a co-ligand.

19. The method of claim 18, wherein the conjugated backbone is synthesized by reaction of a dihalide with a diboronate or diboronic acid in a Suzuki reaction.

20. The method of claim 19, wherein the diboronate or diboronic acid is a derivative of 9,9-disubstituted fluorene or 9-substituted carbazole.

21. The method of claim 19, wherein the dihalide is a derivative of 1,10-phenanthroline, 2,2-bipyridine, 1,3,4-oxadiazole, triphenylamine, 9,9-disubstituted fluorene and 9-substituted carbazole.

22. The method of claim 18, wherein the conjugated backbone is synthesized by a tetrazole condensation reaction comprising reacting a ditetrazole derivative of a 9,9-disubstituted fluorene or a 9-substituted carbazole and a diacyl chloride derivative of 2,2-bipyridine or 1,10-phenanthroline.

23. The method of to claim 18, wherein the co-ligand is a derivative of β-diketone, benzoic acid, benzenesulfonic acid, salicylic acid, or pyridine-2,6- dicarboxylic acid.

24. A method of producing the copolymer complex according to claim 1, comprising forming an organic complex [B(C)] and further reacting the organic complex to A and D to form the copolymer complex.

25. A light-emitting device comprising:
a pair of electrodes including an anode and a cathode, wherein at least one electrode is transparent or semi-transparent; and
a light-emitting layer between the pair of electrodes, wherein the light-emitting layer comprises a copolymer complex of the formula:

wherein $[A_x-[B(C)]_y-D_z]$ denotes a single unit of the copolymer complex that is repeated n times, wherein n is an integer cireater than one, and wherein the single unit comprises a conjugated backbone coordinated to a complex (C) comprising rare earth metal(s); x. y and z are numbers cireater than zero such that x=y+z; A is independently selected from a group consisting of: fluorene, carbazole, oxadiazole, triphenylamine, and derivatives thereof; B is a functional ligand selected from the group consisting of: benzoic acid, 1,3-diphenylpropane-1,3-dione, 1,10-phenanthroline, 2,2-bipyridine, and derivatives thereof; and D is independently selected from the group consisting of: fluorene, carbazole, oxadiazole, triphenylamine, and derivatives thereof.

26. An apparatus comprising a copolymer complex of the formula:

wherein $[A_x-[B(C)]_y-D_z]$ denotes a single unit of the copolymer complex that is repeated n times, wherein n is an integer greater than one, and wherein the single unit comprises a conjugated backbone coordinated to a complex (C) comprising rare earth metal(s): x. y and z are numbers greater than zero such that x=y+z; A is independently selected from a group consisting of: fluorene, carbazole, oxadiazole, triphenylamine, and derivatives thereof; B is a functional ligand selected from the group consisting of: benzoic acid. 1,3-diphenylpropane-1,3-dione, 1,10-phenanthroline, 2,2-bipyridine, and derivatives thereof; and D is independently selected from the group consisting of: fluorene, carbazole, oxadiazole, triphenylamine, and derivatives thereof.

27. The apparatus of claim 26, wherein the apparatus is an optical fiber amplifier, and wherein the copolymer complex includes an erbium, neodymium, or praseodymium complex.

28. The apparatus of claim 26, wherein the apparatus is a photonic laser, and wherein the copolymer complex includes a neodymium complex.

29. The apparatus of claim 26, wherein the apparatus is an electro-optical modulator.

30. The device of claim 25, wherein the device is a polymer light-emitting device or an organic light-emitting device.

31. The device of claim 30, wherein the device is the organic light-emitting device and wherein the light-emitting layer is transparent.

32. The device of claim 25, wherein the light-emitting layer has a thickness from about 0.01 micrometers to 200 micrometers.

33. The device of claim 30, wherein the light-emitting layer is the polymer light-emitting device and has a thickness from about 0.01 micrometers to 200 micrometers.

34. The device of claim 25, wherein the light-emitting layer includes at least one complex selected from a group consisting of europium complex, samarium complex, terbium complex, thulium complex, erbium complex, neodymium complex, and holmium complex.

35. The device of claim 25, wherein the anode is transparent or semi-transparent, wherein the anode comprises a substrate and a film on the substrate, and wherein the film comprises indium oxide, tin oxide, zinc oxide, or a mixture of one or more thereof.

36. The device of claim 25, wherein the cathode comprises aluminum, barium, calcium, magnesium, potassium, lithium, sodium, rubidium, strontium, or an alloy of one or more thereof.

37. The device of claim 36, wherein the cathode comprises the alloy and further comprises one or more of gold, silver, platinum, copper, titanium, nickel, tungsten, indium, or tin.

38. The device of claim 25, further comprising a hole-transporting layer disposed between the anode and the light-emitting layer.

39. The device of claim 25, further comprising an electron-transporting layer disposed between the cathode and the light-emitting layer.

40. The device of claim 25, wherein the light-emitting layer includes a hole-transporting material, an electron-transporting material, or a mixture thereof.

41. The device of claim 25, further comprising a charge injecting layer disposed between the anode and the cathode.

42. The device of claim 41, wherein the charge injecting layer is a conducting polymer selected from a group consisting of polyaniline, polythiophene, polypyrrole, poly(phenylene vinylene), poly(thienylene vinylene), or a derivative of one or more thereof.

43. The device of claim 41, wherein the charge injecting layer is doped with ions selected from a group consisting of polystyrene sulfonate ions, alkylbenzene sulfonate ions, lithium ions, potassium ions, or tetrabutyl ammonium ions.

44. The device of claim 25, further comprising one or more insulating layers, wherein at least one of the insulating layers is disposed adjacent to one of the electrodes.

45. The device of claim 44, wherein the one or more insulating layers comprise a material selected from a group consisting of a metal fluoride, a metal oxide, or a metal phthalocyanine.

46. The device of claim 45, wherein the one or more insulating layers comprise a material selected from a group consisting of lithium fluoride, aluminum oxide, or copper phthalocyanine.

47. The device of claim 25, wherein the device is a display device.

48. The device of claim 25, wherein the device is a segment display or a flat light source.

49. The apparatus of claim 26, wherein the copolymer complex is included in a semiconductor layer, and wherein the apparatus further comprises:
   an insulator layer, wherein the semiconductor layer is adjacent to one surface of the insulator layer;
   a first electrode configured as a source;
   a second electrode configured as a drain, wherein the first and second electrodes are attached to the semiconductor layer; and
   a third electrode configured as a gate and positioned adjacent to another surface of the insulator layer.

* * * * *